(12) United States Patent
Phillips et al.

(10) Patent No.: US 10,113,114 B2
(45) Date of Patent: Oct. 30, 2018

(54) APPARATUS AND METHOD FOR COATING PARTICULATE MATERIAL

(71) Applicant: BASF Corporation, Florham Park, NJ (US)

(72) Inventors: Laura Beth Phillips, Pleasantville, IA (US); Brent Christopher Packer, Ames, IA (US); David Chamberlain Roller, Kokomo, IN (US); Richard Alan Moffitt, Jr., Marion, IA (US); Douglas Edward Grunder, Mt Vernon, IA (US)

(73) Assignee: BASF Corporation, Florham Park, NJ (US)

( * ) Notice: Subject to any disclaimer, the term of this patent is extended or adjusted under 35 U.S.C. 154(b) by 162 days.

(21) Appl. No.: 14/954,706

(22) Filed: Nov. 30, 2015

(65) Prior Publication Data

US 2016/0083651 A1   Mar. 24, 2016

Related U.S. Application Data

(63) Continuation-in-part of application No. 14/785,283, filed as application No. PCT/US2014/035272 on Apr.
(Continued)

(30) Foreign Application Priority Data

May 20, 2013   (EP) ..................................... 13168449

(51) Int. Cl.
*C09K 17/52*   (2006.01)
*A01N 33/18*   (2006.01)
(Continued)

(52) U.S. Cl.
CPC .............. *C09K 17/52* (2013.01); *A01N 25/08* (2013.01); *A01N 25/34* (2013.01); *A01N 33/18* (2013.01);
(Continued)

(58) Field of Classification Search
CPC combination set(s) only.
See application file for complete search history.

(56) References Cited

U.S. PATENT DOCUMENTS 3,735,532 A   5/1973   Long, III
5,714,263 A   2/1998   Jakubisin et al.
(Continued)

FOREIGN PATENT DOCUMENTS

WO   2012109432 A1   8/2012
WO   WO2014/194260   * 12/2014

OTHER PUBLICATIONS

BASF Safety Data Sheet for Freehand herbicide, Nov. 2013.*
(Continued)

*Primary Examiner* — Erma C Cameron
(74) *Attorney, Agent, or Firm* — Armstrong Teasdale LLP

(57) ABSTRACT

In a method of treating a particulate landscaping material, the material is fed into a mixing chamber and an additive mixture including a functional additive and a carrier is delivered to spray nozzles within the mixing chamber. At least one of the spray nozzles is operated to direct an atomized spray into the mixing chamber. The material is agitated within the mixing chamber during and/or after directing the atomized spray into the mixing chamber. The material is then conveyed with the additive mixture applied thereto to a mixing chamber outlet. During these steps, a volumetric flow rate of the particulate landscape material through the mixing chamber is intermittently determined. The determined volumetric flow rate is intermittently com-
(Continued)

pared to a predetermined target flow rate of the particulate landscape material. Based on this comparison, the volumetric flow rate of the particulate landscape material through the mixing chamber is adjusted.

20 Claims, 10 Drawing Sheets

Related U.S. Application Data 24, 2014, application No. 14/954,706, which is a continuation-in-part of application No. PCT/US2015/030998, filed on May 15, 2015.

(60) Provisional application No. 61/993,330, filed on May 15, 2014, provisional application No. 61/816,353, filed on Apr. 26, 2013.

(51) Int. Cl.
| | | |
|---|---|---|
| *A01N 43/10* | (2006.01) | |
| *A01N 53/00* | (2006.01) | |
| *B05D 1/12* | (2006.01) | |
| *A01N 25/08* | (2006.01) | |
| *A01N 47/44* | (2006.01) | |
| *A01N 25/34* | (2006.01) | |
| *A01N 51/00* | (2006.01) | |
| *B05D 1/02* | (2006.01) | |

(52) U.S. Cl.
CPC .............. *A01N 43/10* (2013.01); *A01N 47/44* (2013.01); *A01N 51/00* (2013.01); *A01N 53/00* (2013.01); *B05D 1/12* (2013.01); *B05D 1/02* (2013.01); *B05D 2258/00* (2013.01)

(56) References Cited

U.S. PATENT DOCUMENTS

| | | | |
|---|---|---|---|
| 5,866,201 | A | 2/1999 | Blue |
| 9,950,331 | B2 * | 4/2018 | Phillips .................. B05B 15/25 |
| 2003/0201154 | A1 | 10/2003 | Hallstrom |
| 2004/0228207 | A1 | 11/2004 | McNeff et al. |
| 2011/0152100 | A1 * | 6/2011 | Parrish ............... A01G 13/0275 |
| | | | 504/215 |

OTHER PUBLICATIONS

CAS Registry File for 163515-14-8, Jun. 1995.*
International Search Report and Written Opinion for PCT/US2014/035272, dated Sep. 23, 2014, 8 pages.

* cited by examiner

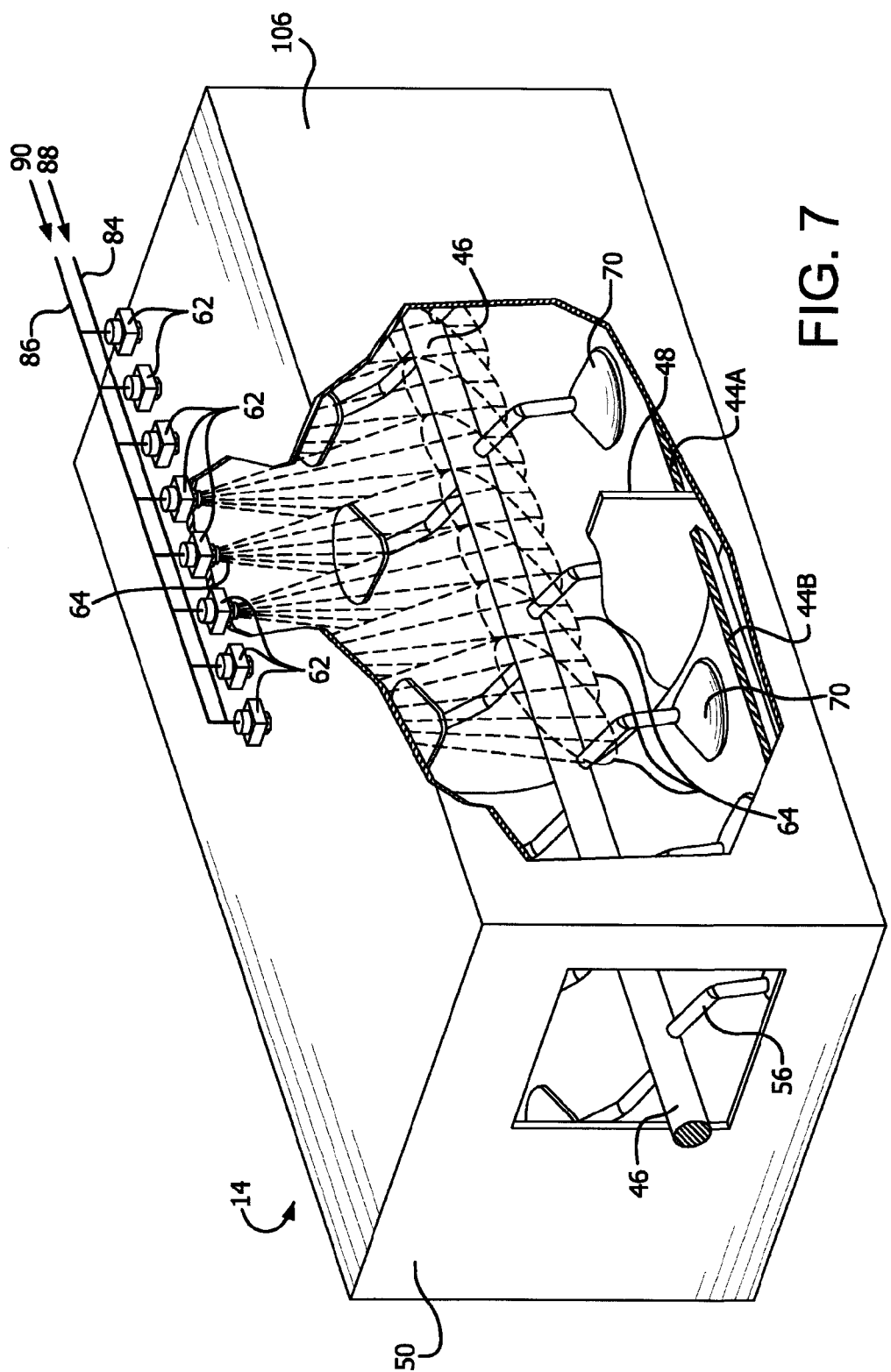

APPARATUS AND METHOD FOR COATING PARTICULATE MATERIAL

CROSS-REFERENCE TO RELATED APPLICATIONS

This application is a continuation-in-part of U.S. patent application Ser. No. 14/785,283, filed Oct. 16, 2015, which is the National Stage entry of PCT International Patent Application No. PCT/US2014/035272, filed Apr. 24, 2014, which claims the benefit of U.S. Provisional Patent Application Ser. No. 61/816,353, filed Apr. 26, 2013, and is also a continuation-in-part of PCT International Patent Application No. PCT/US2015/030998, filed May 15, 2015, which claims the benefit of U.S. Provisional Patent Application Ser. No. 61/993,330, filed May 15, 2014, all of which are incorporated herein by reference.

FIELD OF THE INVENTION

The present disclosure relates to an apparatus and a method for coating a particulate material. The apparatus and method may each in one form be applied to the coating of landscaping materials, such as mulch or potting soil.

BACKGROUND OF THE INVENTION

Apparatus and methods for coating landscaping materials and particulate ground cover materials are known. Winistorfer et al, U.S. Pat. No. 6,551,401, shows and describes a machine for coloring landscaping materials, such as wood mulch and the like. The apparatus in Winistorfer patent may be used for continuous mixing of the colorant with the mulch material within a multistage mixing bowl. The disclosure in this prior patent is incorporated herein by reference.

Greenberg et al. U.S. Pat. No. 5,910,514, describes a colored rubber material formed to simulate wood mulch.

Rondy U.S. Pat. No. 5,192,587 describes the use of a continuous auger screw within an angled trough for applying colorant to mulch materials. Other apparatus and methods are known for coating of materials, including wood and rubber particulate material. Various methods may be performed as a continuous process or on a batch basis.

The modification of landscape materials is even more important when it comes to the functional modification of landscape materials because landscape materials as particulate ground cover materials may be used for improving water retention of the soil and can help to maintain, improve or even restore the fertility of soil thereby contributing to better plant growth and higher crop yields. Accordingly, there is continued interest in improved methods for providing functional treatments of landscape materials.

One important aspect for functional modification of landscape materials is the exact and consistent application of functional materials to landscape materials. It is especially difficult to apply the functional material as uniform as possible to the landscape material. Therefore, improved processes that allow more uniform functional treatment of landscape material would be of great benefit in the field of coating landscape materials.

SUMMARY OF THE INVENTION

In one aspect of the disclosure, a method of applying a functional additive to a particulate landscaping material includes feeding a particulate landscaping material into a mixing chamber and delivering a flow of additive mixture to a plurality of spray nozzles within the mixing chamber. The additive mixture includes a functional additive and a carrier. At least one of the plurality of nozzles is operated to direct an atomized spray of additive mixture into the mixing chamber for contact with particulate landscaping material in the mixing chamber. The particulate landscaping material is agitated within the mixing chamber at least one of during and after directing the atomized spray of additive mixture into the mixing chamber. The particulate landscaping material is conveyed with the additive mixture applied thereto to a mixing chamber outlet. During the feeding, delivering, operating, agitating and conveying steps, a volumetric flow rate of the particulate landscape material through the mixing chamber is intermittently determined. The determined volumetric flow rate of the particulate landscape material is intermittently compared to a predetermined target flow rate of the particulate landscape material. Based on this comparison, the volumetric flow rate of the particulate landscape material through the mixing chamber is adjusted.

As used herein, mulch is referred to as a material that is applied as a layer to the surface of an area of soil, often around or in the vicinity of one or more plants. The mulch can be used to conserve moisture, improve fertility and health of the soil, reduce weed growth, and enhance visual appeal of the area. Potting soil is a mixture of organic material, drainage material, water retention, and pest resistant material, as well as the necessary nutrients that is applied as substrate in which to grow plants. The potting soil can be used to conserve moisture, improve fertility and health of the soil and to provide the optimal growing substrate for plants. For purposes of this application, it is understood that "mulch" means any material applied to the surface of an area of soil for any number of purposes, including plant growth enhancement, moisture conservation, improvement of soil health and fertility, weed growth reduction, or visual appeal enhancement. Mulch can include any type of biodegradable natural fiber, including wood, paper, grass, hay, straw, pellets, organic residues, rubber, plastic, or rock and gravel. In certain embodiments, the mulch can be wood mulch from wood of any type, including hardwood, softwood, or recycled wood. The wood mulch can be ground wood mulch of any grind size or mix of grind sizes or chipped wood mulch of any chip size or mix of chip sizes. The pellet mulch can be made up of natural fiber pellets or any other known pellet for a mulch product. According to certain implementations, the organic residue mulch can be made of grass clippings, leaves, hay, straw, shredded bark, whole bark nuggets, sawdust, shells, woodchips, shredded newspaper, cardboard, or any other known organic residue used in mulch products. In one embodiment, the rubber mulch can be made from recycled tire rubber or any other known type or source of rubber that is used in mulch products. Further, the plastic sheet mulch can be any known mulch product in the form of a plastic sheet, including, for example, the type of plastic sheet mulch used in large-scale vegetable farming. In certain embodiments, mulch is any functional ground cover.

For purposes of this application, it is understood that "potting soil" also known as potting mix, or potting compost, means any material or medium in which to grow plants. Some common ingredients used in potting soil are peat, composted bark, soil, sand, sandy loam (combination of sand, soil and clay), perlite or vermiculate and recycled mushroom compost or other aged compost products although many others are used and the proportions vary hugely. Most commercially available potting soils have their pH fine-tuned with ground limestone, some contain small amounts of fertilizer and slow-release nutrients. Potting soil recipes are known e.g. from US 2004/0089042 A1. Commercially available potting soil is sterilized, in order to avoid the spread of weeds and plant-borne diseases. Packaged potting soil often is sold in bags ranging from 1 to 50 kg.

Other features and combinations of features will become apparent from the detailed description to follow, taken in conjunction with the accompanying drawings.

BRIEF DESCRIPTION OF THE DRAWINGS

For the purpose of illustrating the invention, the drawings show forms that are presently preferred. It should be understood that the invention is not limited to the precise arrangements and instrumentalities shown in the drawings.

For the purpose of illustrating the invention, the drawings show forms that are presently preferred. It should be understood that the invention is not limited to the precise arrangements and instrumentalities shown in the drawings.

FIG. 7 shows a partial, isometric view of a nozzle spray pattern within the mixer portion of the apparatus.

DETAILED DESCRIPTION

Figure 1:
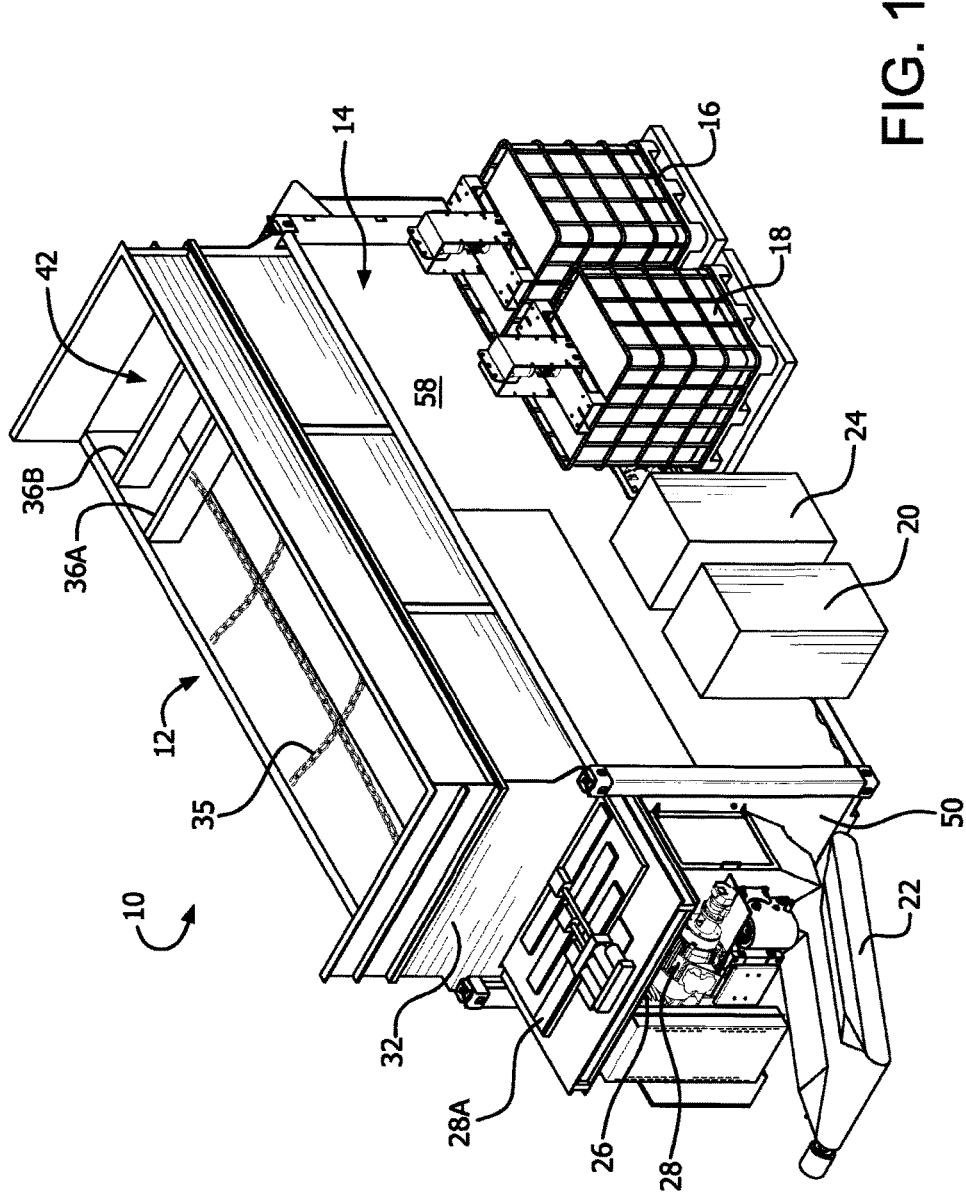
FIG. 1 shows an isometric view of an embodiment of an apparatus for performing a method contemplated by the present disclosure.

In the figures, where like numerals identify like elements, there is shown an embodiment of an apparatus for performing a process for mixing particulate material with a coating. The mixing apparatus is designated generally by the numeral 10 in FIG. 1 and, as illustrated, defines as a continuous process. The apparatus 10 includes feed means 12 for delivering particulate material into a mixer 14. The feed means 12 controls the rate of flow of particulate into the mixer 14. Storage means 16 and 18 are shown positioned adjacent the apparatus 10 for storing and delivering a coating material or constituent parts of a coating mixture. The storage means may be provided in any number of forms, but is typically contemplated to be a barrel, tote or other container. Two storage means are shown. A single container may alternatively be provided or more than two containers may be provided. Other delivery means may be provided for directing a coating to the apparatus 10.

The material stored in the storage means 16, 18 is generally contemplated to be in a liquid or slurry form. Coatings may comprise any material that is applied to the particulate to provide a functional attribute. However, functional materials according to the present invention do not include colorants.

A functional additive or (coating) material may be combined with other coating materials or may form the coating by itself. A functional additive according to the present invention is typically a material that provides a functional attribute, such as encouraging or deterring plant growth, controlling insects or other pests, controlling the advancement of fungi, etc. Preferred functional materials according to the present invention are therefore herbicides, insecticides, nutrients, wetting agents, surfactants, fungicides, biologicals, inoculants and mixtures thereof.

Preferred herbicides to be used in the process according to the present invention include the following substances and mixtures thereof:

acetamides: acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;

amino acid derivatives: bilanafos, glyphosate, glufosinate, sulfosate;

aryloxyphenoxypropionates: clodinafop, cyhalofop-butyl, fenoxaprop, fluazifop, haloxyfop, metamifop, propaquizafop, quizalofop, quizalofop-P-tefuryl;

bipyridyls: diquat, paraquat;

(thio)carbamates: asulam, butylate, carbetamide, desmedipham, dimepiperate, eptam (EPTC), esprocarb, molinate, orbencarb, phenmedipham, prosulfocarb, pyributicarb, thiobencarb, triallate;

cyclohexanediones: butroxydim, clethodim, cycloxydim, profoxydim, sethoxydim, tepraloxydim, tralkoxydim;

dinitroanilines: benfluralin, ethalfluralin, oryzalin, pendimethalin, prodiamine, trifluralin;

diphenyl ethers: acifluorfen, aclonifen, bifenox, diclofop, ethoxyfen, fomesafen, lactofen, oxyfluorfen;

hydroxybenzonitriles: bomoxynil, dichlobenil, ioxynil;

imidazolinones: imazamethabenz, imazamox, imazapic, imazapyr, imazaquin, imazethapyr;

phenoxy acetic acids: clomeprop, 2,4-dichlorophenoxyacetic acid (2,4-D), 2,4-DB, dichlorprop, MCPA, MCPA-thioethyl, MCPB, Mecoprop;

pyrazines: chloridazon, flufenpyr-ethyl, fluthiacet, norflurazon, pyridate; pyridines: aminopyralid, clopyralid, diflufenican, dithiopyr, fluridone, fluroxypyr, picloram, picolinafen, thiazopyr;

sulfonyl ureas: amidosulfuron, azimsulfuron, bensulfuron, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;

triazines: ametryn, atrazine, cyanazine, dimethametryn, ethiozin, hexazinone, metamitron, metribuzin, prometryn, simazine, terbuthylazine, terbutryn, triaziflam;

ureas: chlorotoluron, daimuron, diuron, fluometuron, isoproturon, linuron, methabenzthiazuron, tebuthiuron;

other acetolactate synthase inhibitors: bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam;

others: amicarbazone, aminotriazole, anilofos, beflubutamid, benazolin, bencarbazone, benflure sate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofumesate, etobenzanid, fenoxasulfone, fentrazamide, flumiclorac-pentyl, flumioxazin, flupoxam, flurochloridone, flurtamone, indanofan, isoxaben, isoxaflutole, lenacil, propanil, propyzamide, quinclorac, quinmerac, mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4-fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoropyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester.

Especially preferred herbicides are pendimethalin, dimethenamid and the combination thereof.

The herbicide is preferably present in the functional coating of the particulate material, preferably mulch, in an amount of 0.0001 to 0.1% by weight, more preferably 0.0005 to 0.05% by weight, and even more preferably 0.001 to 0.01% by weight based on the particulate material.

Preferred insecticides to be used in the process according to the present invention include the following substances and mixtures thereof:

organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;

carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;

pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;

insect growth regulators: a) chitin synthesis inhibitors: benzoylureas: chlorfluazuron, cyramazin, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;

nicotinic receptor agonists/antagonists compounds: clothianidin, dinotefuran, flupyradifurone, imidacloprid, thiamethoxam, nitenpyram, acetamiprid, thiacloprid, 1 2-chloro-thiazol-5-ylmethyl)-2-nitrimino-3,5-dimethyl-[1,3,5]triazinane;

GABA antagonist compounds: endosulfan, ethiprole, fipronil, vaniliprole, pyrafluprole, pyriprole, 5-amino-1-(2,6-dichloro-4-methyl-phenyl)-4-sulfinamoyl-1H pyrazole-3-carbothioic acid amide;

macrocyclic lactone insecticides: abamectin, emamectin, milbemectin, lepimectin, spinosad, spinetoram;

mitochondrial electron transport inhibitor (METI) I acaricides: fenazaquin, pyridaben, tebufenpyrad, tolfenpyrad, flufenerim;

METI II and III compounds: acequinocyl, fluacyprim, hydramethylnon;

Uncouplers: chlorfenapyr;

oxidative phosphorylation inhibitors: cyhexatin, diafenthiuron, fenbutatin oxide, propargite;

moulting disruptor compounds: cryomazine;

mixed function oxidase inhibitors: piperonyl butoxide;

sodium channel blockers: indoxacarb, metaflumizone;

ryanodine receptor inhibitors: chlorantraniliprole, cyantraniliprole, flubendiamide, N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; N-[4-chloro-2-[(diethyl-lambda-4-sulfanylidene)carbamoyl]-6-methyl-phenyl]-2-(3-chloro-2-pyridyl)-5-(trifluoromethyl) pyrazole-3-carboxamide; N-[4-chloro-2-[(di-2-propyl-lambda-4-sulfanyli-dene) carbamoyl]-6-methyl-phenyl]-2-(3-chloro-2-pyridyl)-5-(trifluoromethyl)pyrazole-3-carboxamide; N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; N-[4,6-dichloro-2-[(diethyl-lambda-4-sulfanylidene) carbamoyl]-phenyl]-2-(3-chloro-2-pyridyl)-5-(di-fluoromethyl)pyrazole-3-carboxamide; N-[4,6-dibromo-2-[(di-2-propyl-lambda-4-sulfanylidene)carbamoyl]-phenyl]-2-(3-chloro-2-pyridyl)-5-(trifluoromethyl) pyrazole-3-carboxamide; N-[4-chloro-2-[(di-2-propyl-lambda-4-sulfanylidene)carbamoyl]-6-cyanophenyl]-2-(3-chloro-2-pyridyl)-5-(trifluoromethyl)pyrazole-3-carboxamide; N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide; cyazypyr, rynaxapyr;

others: benclothiaz, bifenazate, artap, flonicamid, pyridalyl, pymetrozine, sulfur, thiocyclam, cyenopyrafen, flupyrazofos, cyflumetofen, amidoflumet, imicyafos, bistrifluron, pyrifluquinazon and 1,1'-[(3 S,4R,4aR,6S, 6aS,12R,12aS,12bS)-4-[[(2-cyclopropylacetyl)oxy] methyl]-1,3,4,4a,5,6,6a, 12,12a, 12b-decahydro-12-hydroxy-4,6a, 12b-trimethyl-11-oxo-9-(3-pyridinyl)-2H, 11H-naphtho[2,1-b]pyrano[3,4-e]pyran-3,6-diyl] cyclopropaneacetic acid ester.

Even more preferred insecticides to be used in the process according to the present invention include the following substances and mixtures thereof:

carbamates: methiocarb, thiodicarb;
pyrethroids: bifenthrin, cypermethrin, alpha-cypermethrin, beta-cypermethrin, zeta-cypermethrin, deltamethrin, tefluthrin;
nicotinic receptor agonists/antagonists compounds: clothianidin, dinotefuran, imidacloprid, thiamethoxam, acetamiprid, thiacloprid;
GABA antagonist compounds: fipronil;
ryanodine receptor inhibitors: cyazypyr, rynaxapyr.

The most preferred insecticides to be used in the process according to the present invention include the following substances and mixtures thereof:
carbamates: thiodicarb;
pyrethroids: alpha-cypermethrin;
nicotinic receptor agonists/antagonists compounds: clothianidin, imidacloprid, thiamethoxam, thiacloprid, dinotefuran;
GABA antagonist compounds: fipronil;
ryanodine receptor inhibitors: cyazypyr, rynaxapyr.

The insecticide is preferably present in the functional coating of the particulate material, preferably mulch, in an amount of 0.0001 to 0.1% by weight, more preferably 0.0005 to 0.01% by weight, and even more preferably 0.001 to 0.006% by weight based on the particulate material.

Preferred fungicides to be used in the process according to the present invention include the following substances and mixtures thereof:

A) Respiration Inhibitors:
inhibitors of complex III at Qo site (e. g. strobilurins): azoxystrobin, coumethoxy¬strobin, coumoxystrobin, dimoxystrobin, enestroburin, fenaminstrobin, fenoxystrobin/flufenoxystrobin, fluoxastro¬bin, kresoxim-methyl, mandestrobine, metominostrobin, orysastrobin, picoxystrobin, pyraclostrobin, pyrametostrobin, pyraoxystrobin, trifloxystrobin and 2-(2-(3-(2,6-dichlorophenyl)-1-methyl-allylidene-aminooxymethyl)-phenyl)-2-methoxyimino-N-methyl-acetamide, pyribencarb, triclopyricarb/chlorodincarb, famoxadone, fenamidone;
inhibitors of complex III at Qi site: cyazofamid, amisulbrom, [(3S,6S,7R,8R)-8-benzyl-3-[(3-acetoxy-4-methoxy-pyridine-2-carbonyl)amino]-6-methyl-4,9-dioxo-1,5-dioxonan-7-yl]2-methylpropanoate, [(3S,6S,7R,8R)-8-benzyl-3-[[3-(acetoxymethoxy)-4-methoxy-pyridine-2-carbonyl]amino]-6-methyl-4,9-dioxo-1,5-dioxonan-7-yl]2-methylpropanoate, [(3 S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl]2-methylpropanoate, [(3 S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl]2-methylpropanoate; (3 S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate.
inhibitors of complex II (e.g., carboxamides): benodanil, benzovindiflupyr, bixafen, boscalid, carboxin, fenfuram, fluopyram, flutolanil, fluxapyroxad, furametpyr, isofetamid, iso¬pyrazam, mepronil, oxycarboxin, penflufen, penthiopyrad, sedaxane, tecloftalam, thifluzamide, N-(4'-trifluoromethylthiobiphenyl-2-yl)-3-difluoromethyl-1-methyl-1H-pyrazole-4-carboxamide, N-(2-(1,3,3-trimethyl-butyl)-phenyl)-1,3-dimethyl-5-fluoro-1H-pyrazole-4-carboxamide, 3-(difluoromethyl)-1-methyl-N-(1,1,3-trimethylindan-4-yl)pyrazole-4-carboxamide, 3 (trifluoromethyl)-1-methyl-N-(1,1,3-trimethylindan-4-yl)pyrazole-4-carboxamide, 1,3-dimethyl-N-(1,1,3-trimethylindan-4-yl)pyrazole-4-carboxamide, 3-(trifluoromethyl)-1,5-dimethyl-N-(1,1,3-trimethylindan-4-yl)pyrazole-4-carboxamide, 1,3,5-trimethyl-N-(1,1,3-trimethylindan-4-yl)pyrazole-4-carboxamide, N-(7-fluoro-1,1,3-trimethylindan-4-yl)-1,3-dimethyl-pyrazole-4-carboxamide, N-[2-(2,4-dichlorophenyl)-2-methoxy-1-methyl-ethyl]-3-(difluoromethyl)-1-methyl-pyrazole-4-carboxamide;
other respiration inhibitors (e. g. complex I, uncouplers): diflumetorim, (5,8-difluoro-quinazolin-4-yl)-{2-[2-fluoro-4-(4-trifluoromethylpyridin-2-yloxy)-phenyl]-ethyl}-amine; nitrophenyl derivates: binapacryl, dinobuton, dinocap, fluazinam; ferimzone; organometal compounds: fentin salts, such as fentin-acetate, fentin chloride or fentin hydroxide; ametoctradin; and silthiofam;

B) Sterol Biosynthesis Inhibitors (SBI Fungicides):
C14 demethylase inhibitors (DMI fungicides): triazoles: azaconazole, bitertanol, bromuconazole, cyproconazole, difenoconazole, diniconazole, diniconazole-M, epoxiconazole, fenbuconazole, fluquinconazole, flusilazole, flutriafol, hexaconazole, imibenconazole, ipconazole, metconazole, myclobutanil, oxpoconazole, paclobutrazole, penconazole, propiconazole, prothioconazole, simeconazole, tebuconazole, tetraconazole, triadimefon, triadimenol, triticonazole, uniconazole, 1-[rel-(2S;3R)-3-(2-chlorophenyl)-2-(2,4-difluorophenyl)-oxiranylmethyl]-5-thiocyanato-1H-[1,2,4]triazole, 2-[rel-(2S;3R)-3-(2-chlorophenyl)-2-(2,4-difluorophenyl)-oxiranyl-methyl]-2H-[1,2,4]triazole-3-thiol, 2-[2-chloro-4-(4-chlorophenoxy)phenyl]-1-(1,2,4-triazol-1-yl)pentan-2-ol, 1-[4-(4-chlorophenoxy)-2-(trifluoromethyl)phenyl]-1 cyclopropyl-2-(1,2,4-triazol-1-yl)ethanol, 2-[4-(4-chlorophenoxy)-2-(trifluoromethyl)phenyl]-1-(1,2,4-triazol-1-yl)butan-2-ol, 2-[2-chloro-4-(4-chlorophenoxy)phenyl]-1-(1,2,4-triazol-1-yl)butan-2-ol, 2-[4-(4-chlorophenoxy)-2-(trifluoromethyl)phenyl]-3-methyl-1-(1,2,4-triazol-1-yl)butan-2-ol, 2-[4-(4-chlorophenoxy)-2-(trifluoromethyl)-phenyl]-1-(1,2,4-triazol-1-yl)propan-2-ol, 2-[2-chloro-4-(4-chlorophenoxy)phenyl]-3-methyl-1-(1,2,4-triazol-1-yl)butan-2-ol, 2-[4-(4-chlorophenoxy)-2-(trifluoromethyl)-phenyl]-1-(1,2,4-triazol-1-yl)pentan-2-ol, 2-[4-(4-fluorophenoxy)-2-(trifluoromethyl)-phenyl]-1-(1,2,4-triazol-1-yl)propan-2-ol, 2-[2-chloro-4-(4-chlorophenoxy)phenyl]-1-(1, 2,4-triazol-1-yl)pent-3-yn-2-ol; imidazoles: imazalil, pefurazoate, prochloraz, triflumizol; pyrimidines, pyridines and piperazines: fenarimol, nuarimol, pyrifenox, triforine, [3-(4-chloro-2-fluoro-phenyl)-5-(2,4-difluorophenyl)isoxazol-4-yl]-(3-pyridyl)methanol;
Delta14-reductase inhibitors: aldimorph, dodemorph, dodemorph-acetate, fenpropimorph, tridemorph, fenpropidin, piperalin, spiroxamine;
Inhibitors of 3-keto reductase: fenhexamid;

C) Nucleic Acid Synthesis Inhibitors:
phenylamides or acyl amino acid fungicides: benalaxyl, benalaxyl-M, kiralaxyl, metalaxyl, metalaxyl-M (mefenoxam), ofurace, oxadixyl;
others: hymexazole, octhilinone, oxolinic acid, bupirimate, 5-fluorocytosine, 5-fluoro-2-(p-tolylmethoxy)pyrimidin-4-amine, 5-fluoro-2-(4-fluorophenylmethoxy)pyrimidin-4 amine;

D) Inhibitors of Cell Division and Cytoskeleton:
tubulin inhibitors, such as benzimidazoles, thiophanates: benomyl, carbendazim, fuberidazole, thiabendazole, thiophanate-methyl; triazolopyrimidines: 5-chloro-7-(4 methylpiperidin-1-yl)-6-(2,4,6-trifluorophenyl)-[1,2,4] triazolo[1,5-a]pyrimidine;
other cell division inhibitors: diethofencarb, ethaboxam, pencycuron, fluopicolide, zoxamide, metrafenone, pyriofenone.

E) Inhibitors of Amino Acid and Protein Synthesis:
methionine synthesis inhibitors (anilino-pyrimidines): cyprodinil, mepanipyrim, pyrimethanil;
protein synthesis inhibitors: blasticidin-S, kasugamycin, kasugamycin hydrochloride-hydrate, mildiomycin, streptomycin, oxytetracyclin, polyoxine, validamycin A.

F) Signal Transduction Inhibitors:
MAP/histidine kinase inhibitors: fluoroimid, iprodione, procymidone, vinclozolin, fenpiclonil, fludioxonil;
G protein inhibitors: quinoxyfen;

G) Lipid and Membrane Synthesis Inhibitors:
Phospholipid biosynthesis inhibitors: edifenphos, iprobenfos, pyrazophos, isoprothiolane;
lipid peroxidation: dicloran, quintozene, tecnazene, tolclofos-methyl, biphenyl, chloroneb, etridiazole;
phospholipid biosynthesis and cell wall deposition: dimethomorph, flumorph, mandipropamid, pyrimorph, benthiavalicarb, iprovalicarb, valifenalate and N-(1-(1-(4-cyano-phenyl¬ethanesulfonyl)-but-2-yl) carbamic acid-(4-fluorophenyl) ester;
compounds affecting cell membrane permeability and fatty acides: propamocarb, propamocarb-hydrochloride
fatty acid amide hydrolase inhibitors: oxathiapiprolin, 2-{3-[2-(1-{[3,5-bis(difluoromethyl-1H-pyrazol-1-yl] acetyl}piperidin-4-yl)-1,3-thiazol-4-yl]-4,5-dihydro-1,2-oxazol-5-yl}phenylmethanesulfonate, 2-{3-[2-(1-{[3,5-bis(difluoromethyl)-1H-pyrazol-1-yl] acetyl}piperidin-4-yl) 1,3-thiazol-4-yl]-4,5-dihydro-1,2-oxazol-5-yl}-3-chlorophenyl methanesulfonate.

H) Inhibitors with Multi Site Action:
inorganic active substances: Bordeaux mixture, copper acetate, copper hydroxide, copper oxychloride, basic copper sulfate, sulfur;
thio- and dithiocarbamates: ferbam, mancozeb, maneb, metam, metiram, propineb, thiram, zineb, ziram;
organochlorine compounds (e. g. phthalimides, sulfamides, chloronitriles): anilazine, chlorothalonil, captafol, captan, folpet, dichlofluanid, dichlorophen, hexachlorobenzene, pentachlorphenole and its salts, phthalide, tolylfluanid, N-(4-chloro-2-nitro-phenyl)-N-ethyl-4-methyl-benzenesulfonamide;
guanidines and others: guanidine, dodine, dodine free base, guazatine, guazatine-acetate, iminoctadine, iminoctadine-triacetate, iminoctadine-tris(albesilate), dithianon, 2,6-dimethyl-1H,5H-[1,4]dithiino[2,3-c:5,6-c']dipyrrole-1,3,5,7(2H,6H)-tetraone.

I) Cell Wall Synthesis Inhibitors:
inhibitors of glucan synthesis: validamycin, polyoxin B;
melanin synthesis inhibitors: pyroquilon, tricyclazole, carpropamid, dicyclomet, fenoxanil;

J) Plant Defence Inducers:
acibenzolar-S-methyl, probenazole, isotianil, tiadinil, prohexadione-calcium; phosphonates: fosetyl, fosetyl-aluminum, phosphorous acid and its salts;

K) Unknown Mode of Action:
bronopol, chinomethionat, cyflufenamid, cymoxanil, dazomet, debacarb, diclomezine, difenoquat, difenzoquat-methylsulfate, diphenylamin, fenpyrazamine, flumetover, flusulfamide, flutianil, methasulfocarb, nitrapyrin, nitrothal-isopropyl, oxathiapiprolin, picarbutrazox, tolprocarb, 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl) piperidin-1-yl]ethanone, 2-[3,5-bis(difluoromethyl)-1H-pyrazol-1-yl]-1-[4-(4-{5-[2-fluoro-6-(prop-2-yn-1-yl¬oxy)phenyl]-4,5-dihydro-1,2-oxazol-3-yl}-1,3-thiazol-2-yl)piperidin-1-yl]ethanone, 2-[3,5-bis(difluoromethyl)-1H-pyrazol-1-yl]-1-[4-(4-{5-[2-chloro-6-(prop-2-yn-1-yl-oxy)phenyl]-4,5-dihydro-1,2-oxazol-3-yl}-1,3-thiazol-2-yl)piperidin-1-yl] ethanone, oxin-copper, proquinazid, tebufloquin, tecloftalam, triazoxide, 2 butoxy-6-iodo-3 propyl-chromen-4-one, N-(cyclopropylmethoxyimino-(6-difluoro-methoxy-2,3-difluoro-phenyl)-methyl)-2-phenyl acetamide, N'-(4-(4-chloro-3-trifluoromethyl-phenoxy)-2,5-dimethyl-phenyl)-N-ethyl-N methyl formamidine, N'-(4-(4-fluoro-3-trifluoromethyl-phenoxy)-2,5-dimethyl-phenyl)-N-ethyl-N-methyl formamidine, N'-(2-methyl-5-trifluoromethyl-4-(3-trimethylsilanyl-propoxy)-phenyl)-N-ethyl-N-methyl formamidine, N'-(5-difluoromethyl-2-methyl-4-(3-trimethylsilanyl-propoxy)-phenyl)-N-ethyl-N-methyl formamidine, methoxy-acetic acid 6-tert-butyl-8-fluoro-2,3-dimethyl-quinolin-4-yl ester, 3-[5-(4-methylphenyl)-2,3-dimethyl-isoxazolidin-3-yl]-pyridine, 3-[5-(4-chlorophenyl)-2,3-dimethyl-isoxazolidin-3-yl]-pyridine (pyrisoxazole), N-(6-methoxy-pyridin-3-yl)cyclopropanecarboxylic acid amide, 5-chloro-1 (4,6-dimethoxy-pyrimidin-2-yl)-2-methyl-1H-benzoimidazole, 2-(4-chloro-phenyl)-N-[4-(3,4-dimethoxy-phenyl)-isoxazol-5-yl]-2-prop-2-ynyloxy-acetamide, ethyl(Z)-3 amino-2-cyano-3-phenyl-prop-2-enoate, pentyl N-[6-[[(Z)-[(1-methyltetrazol-5-yl)-phenyl-methylene]amino]oxymethyl]-2-pyridyl]carbamate, 2-[2-[(7,8-difluoro-2-methyl-3-quinolyl)oxy]-6-fluoro-phenyl]propan-2-ol, 2-[2-fluoro-6-[(8-fluoro-2-methyl-3-quinolyl)oxy]phenyl]propan-2-ol, 3-(5-fluoro-3,3,4,4-tetramethyl-3,4-dihydroisoquinolin-1-yl)quinoline, 3-(4,4-difluoro-3,3-dimethyl-3,4-dihydroisoquinolin-1-yl)quinoline, 3-(4,4,5-trifluoro-3,3-dimethyl-3,4-dihydroisoquinolin-1-yl)quinolone, 9-fluoro-2,2-dimethyl-5-(3-quinolyl)-3H-1,4-benzoxazepine.

Even more preferred fungicides to be used in the process according to the present invention include the following substances and mixtures thereof:

A) Respiration Inhibitors:
Inhibitors of complex III at Qo site (e. g. strobilurins): azoxystrobin, picoxystrobin, pyraclostrobin, trifloxystrobin;
inhibitors of complex III at Qi site: cyazofamid;
inhibitors of complex II (e. g. carboxamides): boscalid, fluopyram, fluxapyroxad, penflufen, penthiopyrad, sedaxane;
other respiration inhibitors: fluazinam;

B) Sterol Biosynthesis Inhibitors (SBI Fungicides):
C14 demethylase inhibitors (DMI fungicides): cyproconazole, difenoconazole, flutriafol, ipconazole, prothio¬conazole, tebuconazole, triticonazole, prochloraz;
Delta14-reductase inhibitors: fenpropimorph;

C) Nucleic Acid Synthesis Inhibitors:
phenylamides or acyl amino acid fungicides: metalaxyl, metalaxyl-M (mefenoxam), ofurace, oxadixyl;
5-fluoro-2-(4-fluorophenylmethoxy)pyrimidin-4 amine;

D) Inhibitors of Cell Division and Cytoskeleton:
tubulin inhibitors, such as benzimidazoles, thiophanates: carbendazim, thiabendazole;
other cell division inhibitors: diethofencarb, ethaboxam, fluopicolide, zoxamide, metrafenone;
F) Signal Transduction Inhibitors:
MAP/histidine kinase inhibitors: fludioxonil;
G protein inhibitors: quinoxyfen;
G) Lipid and Membrane Synthesis Inhibitors:
phospholipid biosynthesis and cell wall deposition: dimethomorph, mandipropamid;
fatty acid amide hydrolase inhibitors: oxathiapiprolin;
H) Inhibitors with Multi Site Action:
thio- and dithiocarbamates: mancozeb, maneb, metam, metiram, thiram, ziram;
organochlorine compounds (e. g. phthalimides, sulfamides, chloronitriles): anilazine, chlorothalonil;
I) Unknown Mode of Action:
cyflufenamid, dazomet, nitrapyrin, oxathiapiprolin.

The most preferred fungicides to be used in the process according to the present invention include the following substances and mixtures thereof:
A) Respiration Inhibitors:
Inhibitors of complex III at Qo site (e. g. strobilurins): azoxystrobin, pyraclostrobin, trifloxystrobin;
inhibitors of complex II (e. g. carboxamides): boscalid, fluopyram, fluxapyroxad, penflufen, penthiopyrad, sedaxane;
B) Sterol Biosynthesis Inhibitors (SBI Fungicides):
C14 demethylase inhibitors (DMI fungicides): difenoconazole, ipconazole, prothio-conazole, triticonazole;
C) Nucleic Acid Synthesis Inhibitors:
phenylamides or acyl amino acid fungicides: metalaxyl, metalaxyl-M (mefenoxam);
D) Inhibitors of Cell Division and Cytoskeleton:
tubulin inhibitors, such as thiabendazole;
other cell division inhibitors: ethaboxam;
G) Lipid and Membrane Synthesis Inhibitors:
fatty acid amide hydrolase inhibitors: oxathiapiprolin;
H) Inhibitors with Multi Site Action:
thio- and dithiocarbamates: mancozeb;
organochlorine compounds (e. g. phthalimides, sulfamides, chloronitriles): chlorothalonil;
I) Unknown Mode of Action:
nitrapyrin, oxathiapiprolin;

The fungicide is preferably present in the functional coating of the particulate material, preferably mulch, in an amount of 0.0001 to 0.1% by weight, more preferably 0.0005 to 0.05% by weight, and even more preferably 0.001 to 0.01% by weight based on the particulate material.

Inoculant compositions according to the present invention comprise microorganisms which have a beneficial effect on plants, preferably the growth of plants. Preferred inoculants to be used in the process according to the present invention include compositions comprising the following microorganisms and combinations thereof:

Bacteria of the genera *Rhizobium, Bradyrhizobium, Sinorhizobium, Mesorhizobium, Pseudomonas, Serratia, Bacillus, Paenibacillus, Pasteuria, Azotobacter, Enterobacter, Azospirillum, Methylobacterium, Cyanobacteria* (blue-green algae), and mycorrhizal fungae. Preferred biologicals to be used in the process according to the present invention include the following substances and mixtures thereof:

Biochemical compounds selected from the groups consisting of geraniol, cuminaldehyde, vanillin, borneol, menthol, anethole, terpineol, limonene, citronellol, eugenol, isoeugenol, linalool, phenylethyl alcohol, most preferably geraniol, Quillay extract-based products (e.g. QL Agri 35, BASF SE), *Agrobacterium radiobacter* K1026 (e. g. NoGall® from BASF Agricultural Specialties Pty Ltd, Australia), *A. radiobacter* K84(Nature 280, 697-699, 1979; e. g. GallTroll® from AG Biochem, Inc., C, USA), *Ampelomyces quisqualis* M-10 (e. g. AQ 10® from Intrachem Bio GmbH & Co. KG, Germany), *Ascophyllum nodosum* (Norwegian kelp, Brown kelp) extract or filtrate (e. g. ORKA GOLD from BASF Agricultural Specialities (Pty) Ltd., South Africa; or Goemar® from Laboratoires Goemar, France), *Aspergillus flavus* NRRL 21882 isolated from a peanut in Georgia in 1991 by USDA, National Peanut Research Laboratory (e. g. in Afla-Guard® from Syngenta, CH), mixtures of *Aureobasidium pullulans* DSM 14940 and DSM 14941 (e. g. blastospores in BlossomProtect® from bio-ferm GmbH, Germany), *Bacillus amyloliquefaciens, Bacillus amyloliquefaciens* FZB42 (e. g. in RhizoVital® 42 from AbiTEP GmbH, Berlin, Germany), *B. amyloliquefaciens* IN937a (J. Microbiol. Biotechnol. 17(2), 280-286, 2007; e. g. in BioYield® from Gustafson LLC, TX, USA), *B. amyloliquefaciens* IT-45 (CNCM I 3800) (e. g. Rhizocell C from ITHEC, France), *B. amyloliquefaciens* TJ1000 (also called 1BE; ATCC BAA-390; e.g. QuickRoots™ from TJ Technologies, Watertown, S. Dak., USA; CA 2471555 A1), *B. amyloliquefaciens* ssp. *plantarum* MBI600 (NRRL B-50595, deposited at USDA) (e. g. Integral®, Subtilex® NG from BASF Corp., USA), *B. cereus* CNCM I-1562 (U.S. Pat. No. 6,406,690), *B. firmus* CNCM I-1582 (WO 2009/126473, WO 2009/124707, U.S. Pat. No. 6,406,690; Votivo® from Bayer Crop Science LP, USA), *Bacillus pumilus, B. pumilus* GB34 (ATCC 700814; e. g. in YieldShield® from Gustafson LLC, TX, USA), and *Bacillus pumilus* KFP9F (NRRL B-50754) (e. g. in BAC-UP or FUSION-P from BASF Agricultural Specialities (Pty) Ltd., South Africa), *B. pumilus* QST 2808 (NRRL B 30087) (e. g. Sonata® and Ballad® Plus from AgraQuest Inc., USA), *Bacillus subtilis, B. subtilis* strain FB17 [was originally isolated from red beet roots in North America (System Appl. Microbiol 27 (2004) 372-379, incorporated herein by reference); deposited at American Type Culture Collection (ATCC), Manassas, Va., USA, under accession number PTA-11857 on Apr. 26, 2011; FB17 strain is also referred to as UD1022 or UD10-22 in some publications], *B. subtilis* CX-9060 (Federal Register 77(7), 1633-1637; Certis U.S.A., L.L.C.), *B. subtilis* GB03 (e. g. Kodiak® or BioYield® from Gustafson, Inc., USA; or Companion® from Growth Products, Ltd., White Plains, N.Y. 10603, USA), *B. subtilis* GB07 (Epic® from Gustafson, Inc., USA), *B. subtilis* QST-713 (NRRL B 21661 in Rhapsody®, Serenade® MAX and Serenade® ASO from AgraQuest Inc., USA), *B. subtilis* var. *amyloliquefaciens* FZB24 (e. g. Taegro® from Novozyme Biologicals, Inc., USA), *B. subtilis* var. *amyloliquefaciens* D747 (FERM BP-8234; KR 100903253; e. g. Double Nickel™ 55 WDG or Double Nickel™ LC from Certis LLC, USA), *Bacillus thuringiensis, B. thuringiensis* ssp. *aizawai* ABTS-1857 (e. g. in XenTari® from BioFa AG, Münsingen, Germany), B. t. ssp. *aizawai* SAN 401 I, ABG-6305 and ABG-6346, *Bacillus* t. ssp. *israelensis* AM65-52 (e. g. in VectoBac® from Valent BioSciences, IL, USA), *Bacillus thuringiensis* ssp. kurstaki SB4 (NRRL B-50753; e. g. Beta Pro® from BASF Agricultural Specialities (Pty) Ltd., South Africa), B. t. ssp. kurstaki ABTS-351 identical to HD-1 (ATCC SD-1275; e. g. in Dipel® DF from Valent BioSciences, IL, USA), B. t. ssp. kurstaki EG 2348 (e. g. in Lepinox® or Rapax® from CBC (Europe) Sid., Italy), B. t. ssp. tenebrionis DSM 2803 (EP 0

585 215 B1; identical to NRRL B-15939; Mycogen Corp.), B. t. ssp. tenebrionis NB-125 (DSM 5526; EP 0 585 215 B1; also referred to as SAN 418 I or ABG-6479; former production strain of Novo-Nordisk), B. t. ssp. tenebrionis NB-176 (or NB-176-1; a gamma-irridated, induced high-yielding mutant of strain NB-125; DSM 5480; EP 585 215 Bl; Novodor® from Valent BioSciences, Switzerland), *Beauveria bassiana* ATCC 74040 (e. g. in Naturalis® from CBC (Europe) S.r.l., Italy), *B. bassiana* DSM 12256 (US 200020031495; e. g. BioExpert® SC from Live Sytems Technology S.A., Colombia), *B. bassiana* GHA (BotaniGard® 22WGP from Laverlam Int. Corp., USA), *B. bassiana* PPRI 5339 (ARSEF number 5339 in the USDA ARS collection of entomopathogenic fungal cultures; NRRL 50757) (e. g. BroadBand® from BASF Agricultural Specialities (Pty) Ltd., South Africa), *B. brongniartii* (e. g. in Melocont® from Agrifutur, Agrianello, Italy, for control of cockchafer; J. Appl. Microbiol. 100(5), 1063-72, 2006), *Bradyrhizobium* sp. (e. g. Vault® from BASF Corp., USA), *B. japonicum* (e. g. VAULT® from BASF Corp., USA), *Burkholderia* sp. A396 (NRRL B-50319; WO 2013/032693; Marrone Bio Innovations, Inc., USA), *Candida oleophila* 1-182 (NRRL Y-18846; e. g. Aspire® from Ecogen Inc., USA, Phytoparasitica 23(3), 231-234, 1995), *C. oleophila* strain O (NRRL Y-2317; Biological Control 51, 403-408, 2009), *Candida saitoana* (e. g. Biocure® (in mixture with lysozyme) and BioCoat® from Micro Flo Company, USA (BASF SE) and Arysta), chitosan (e. g. Armour-Zen® from BotriZen Ltd., NZ), *Clonostachys rosea* f. *catenulata*, also named *Gliocladium catenulatum* (e. g. isolate J 1446: Prestop® from Verdera Oy, Finland), Chromobacterium subtsugae PRAA4-1 isolated from soil under an eastern hemlock (*Tsuga canadensis*) in the Catoctin Mountain region of central Maryland (e. g. in GRANDEVO from Marrone Bio Innovations, USA), *Coniothyrium minitans* CON/M/91-08 (DSM 9660; e. g. Contans® WG, Intercept® WG from Prophyta Biologischer Pflanzenschutz GmbH, Germany; WO 1996/021358), *Cryphonectria parasitica* (e. g. product Endothia parasitica from CNICM, France), *Cryptococcus albidus* (e. g. YIELD PLUS® from Anchor Bio-Technologies, South Africa), *Cryptophlebia leucotreta* granulovirus (Cr1eGV) (e. g. in CRYPTEX from Adermatt Biocontrol, Switzerland), *Cydia pomonella* granulovirus (CpGV) V03 (DSM GV-0006; e. g. in MADEX Max from Andermatt Biocontrol, Switzerland), CpGV V22 (DSM GV-0014; e. g. in MADEX Twin from Adermatt Biocontrol, Switzerland), *Delftia acidovorans* RAY209 (ATCC PTA-4249; WO 2003/57861; e. g. in BIOBOOST from Brett Young, Winnipeg, Canada), *Dilophosphora alopecuri* (Twist Fungus from BASF Agricultural Specialties Pty Ltd, Australia), *Ecklonia maxima* (kelp) extract (e. g. KELPAK SL from Kelp Products Ltd, South Africa), *Flavobacterium* sp. H492 (ATCC B-505584, WO 2013/138398), formononetin (e. g. in MYCONATE from Plant Health Care plc, U.K.), *Fusarium oxysporum* (e. g. BIOFOX® from S.I.A.P.A., Italy, FUSACLEAN® from Natural Plant Protection, France), *Glomus intraradices* (e. g. MYC 4000 from ITHEC, France), *Glomus intraradices* RTI-801 (e. g. MYKOS from Xtreme Gardening, USA or RTI Reforestation Technologies International; USA), grapefruit seeds and pulp extract (e. g. BC-1000 from Chemie S.A., Chile), harpin (alpha-beta) protein (e. g. MESSENGER or HARP-N Tek from Plant Health Care plc, U.K.; Science 257, 1-132, 1992), *Helicoverpa armigera* nucleopolyhedrovirus (HearNPV) (e.g. in HELICOVEX from Adermatt Biocontrol, Switzerland), *Heterorhabditis bacteriophaga* (e. g. Nemasys® G from BASF Agricultural Specialities Limited, UK), Isaria fumosorosea Apopka-97 (ATCC 20874) (PFR-97TM from Certis LLC, USA), cis-jasmone (U.S. Pat. No. 8,221,736), laminarin (e. g. in VACCIPLANT from Laboratoires Goemar, St. Malo, France or Stähler SA, Switzerland), *Lecanicillium longisporum* KV42 and KV71 (e. g. VERTALEC® from Koppert BV, Netherlands), *L. muscarium* KV01 (formerly *Verticillium lecanii*) (e. g. MYCOTAL from Koppert BV, Netherlands), *Lysobacter antibioticus* 13-1 (Biological Control 45, 288-296, 2008), *L. antibioticus* HS124 (Curr. Microbiol. 59(6), 608-615, 2009), *L. enzymogenes* 3.1T8 (Microbiol. Res. 158, 107-115; Biological Control 31(2), 145-154, 2004), *Metarhizium anisopliae* var. *acridum* IMI 330189 (isolated from *Ornithacris cavroisi* in *Niger*; NRRL 50758) (e. g. GREEN MUSCLE® from BASF Agricultural Specialities (Pty) Ltd., South Africa), M. a. var. *acridum* FI-985 (e. g. GREEN GUARD® SC from BASF Agricultural Specialties Pty Ltd, Australia), *M. anisopliae* FI-1045 (e. g. BIOCANE® from BASF Agricultural Specialties Pty Ltd, Australia), *M. anisopliae* F52 (DSM 3884, ATCC 90448; e. g. MET52® Novozymes Biologicals BioAg Group, Canada), *M. anisopliae* ICIPE 69 (e. g. METATHRIPOL from ICIPE, Nairobe, Kenya), *Metschnikowia fructicola* (NRRL Y-30752; e. g. SHEMER® from Agrogreen, Israel, now distributed by Bayer CropSciences, Germany; U.S. Pat. No. 6,994,849), *Microdochium dimerum* (e. g. ANTIBOT® from Agrauxine, France), *Microsphaeropsis ochracea* P130A (ATCC 74412 isolated from apple leaves from an abandoned orchard, St-Joseph-du-Lac, Quebec, Canada in 1993; Mycologia 94(2), 297-301, 2002), *Muscodor albus* QST 20799 originally isolated from the bark of a cinnamon tree in Honduras (e. g. in development products Muscudor™ or QRD300 from AgraQuest, USA), Neem oil (e.g. TRILOGY®, TRIACT® 70 EC from Certis LLC, USA), *Nomuraea rileyi* strains SA86101, GU87401, SR86151, CG128 and VA9101, *Paecilomyces fumosoroseus* FE 9901 (e. g. NO FLY™ from Natural Industries, Inc., USA), *P. lilacinus* 251 (e. g. in BioAct®/MeloCon® from Prophyta, Germany; Crop Protection 27, 352-361, 2008; originally isolated from infected nematode eggs in the Philippines), *P. lilacinus* DSM 15169 (e. g. NEMATA® SC from Live Systems Technology S.A., Colombia), *P. lilacinus* BCP2 (NRRL 50756; e. g. PL GOLD from BASF Agricultural Specialities (Pty) Ltd., South Africa), mixture of *Paenibacillus alvei* NAS6G6 (NRRL B-50755) and *Bacillus pumilus* (e.g. BAC-UP from BASF Agricultural Specialities (Pty) Ltd., South Africa), *Pantoea vagans* (formerly *agglomerans*) C9-1 (originally isolated in 1994 from apple stem tissue; BlightBan C9-1® from NuFrams America Inc., USA, for control of fire blight in apple; J. Bacteriol. 192(24) 6486-6487, 2010), *Pasteuria* sp. ATCC PTA-9643 (WO 2010/085795), *P. nishizawae* Pn1 (e.g. CLARIVA PN from Syngenta Crop Protection, LLC, Greenborom; C, USA), *Pasteuria* sp. ATCC SD-5832 (WO 2012/064527), *P. nishizawae* (WO 2010/80169), *P. penetrans* (U.S. Pat. No. 5,248,500), *P. ramose* (WO 2010/80619), *P. thornea* (WO 2010/80169), *P. usgae* (WO 2010/80169), *Penicillium bilaiae* (e. g. Jump Start® from Novozymes Biologicals BioAg Group, Canada, originally isolated from soil in southern Alberta; Fertilizer Res. 39, 97-103, 1994), *Phlebiopsis gigantea* (e. g. RotStop® from Verdera Oy, Finland), *Pichia anomala* WRL-076 (NRRL Y-30842; U.S. Pat. No. 8,206,972), potassium bicarbonate (e. g. Amicarb® from Stähler S A, Switzerland), Pseudozyma flocculosa PF-A22 UL (e. g. Sporodex® from Plant Products Co. Ltd., Canada), *Pseudomonas* sp. DSM 13134 (WO 2001/40441, e. g. in PRORADIX from Sourcon Padena GmbH & Co. KG, Hechinger Str. 262, 72072

Tübingen, Germany), *P. chloraphis* MA 342 (e. g. in CER-ALL or CEDEMON from BioAgri AB, Uppsala, Sweden), *P. fluorescens* CL 145A (e. g. in ZEQUANOX from Marrone BioInnovations, Davis, Calif., USA; J. Invertebr. Pathol. 113(1):104-14, 2013), *Pythium oligandrum* DV 74 (ATCC 38472; e. g. POLYVERSUM® from Remeslo SSRO, Biopreparaty, Czech Rep. and GOWAN, USA; US 2013/0035230), *Reynoutria sachlinensis* extract (e. g. REGALIA® SC from Marrone BioInnovations, Davis, Calif., USA), *Rhizobium leguminosarum* bv. *phaseoli* (e. g. RHIZO-STICK from BASF Corp., USA), R. 1. bv. *trifolii* RP113-7 (e. g. DORMAL from BASF Corp., USA; Appl. Environ. Microbiol. 44(5), 1096-1101), R. 1. bv. *viciae* P1NP3Cst (also referred to as 1435; New Phytol. 179(1), 224-235, 2008; e. g. in NODULATOR PL Peat Granule from BASF Corp., USA; or in NODULATOR XL PL from BASF Agricultural Specialties Ltd., Canada), R. 1. bv. *viciae* SU303 (e. g. NODULAID Group E from BASF Agricultural Specialties Pty Ltd, Australia), R. 1. bv. *viciae* WSM1455 (e. g. NODULAID Group F from BASF Agricultural Specialties Pty Ltd, Australia), *Sinorhizobium meliloti* MSDJ0848 (INRA, France) also referred to as strain 2011 or RCR2011 (Mol. Gen. Genomics 272, 1-17, 2004; e. g. DORMAL ALFALFA from BASF Corp., USA; NITRAGIN® Gold from Novozymes Biologicals BioAg Group, Canada), *Sphaerodes mycoparasitica* IDAC 301008-01 (WO 2011/022809), *Spodoptera littoralis* nucleopolyhedrovirus (SpliNPV) (e.g. in LITTOVIR from Adermatt Biocontrol, Switzerland), *Steinernema carpocapsae* (e. g. MILLENIUM® from BASF Agricultural Specialities Limited, UK), *S. feltiae* (NEMASHIELD® from BioWorks, Inc., USA; NEMASYS® from BASF Agricultural Specialities Limited, UK), *S. kraussei* L137 (NEMASYS® L from BASF Agricultural Specialities Limited, UK), *Streptomyces griseoviridis* K61 (e. g. MYCOSTOP® from Verdera Oy, Espoo, Finland; Crop Protection 25, 468-475, 2006), *S. lydicus* WYEC 108 (e. g. Actinovate® from Natural Industries, Inc., USA, U.S. Pat. No. 5,403,584), *S. violaceusniger* YCED-9 (e. g. DT-9® from Natural Industries, Inc., USA, U.S. Pat. No. 5,968,503), *Talaromyces flavus* V117b (e. g. PROTUS® from Prophyta, Germany), *Trichoderma asperellum* SKT-1 (e. g. ECO-HOPE® from Kumiai Chemical Industry Co., Ltd., Japan), *T. asperellum* ICC 012 (e. g. in TENET WP, REMDIER WP, BIOTEN WP from Isagro N.C., USA, BIO-TAM from AgraQuest, USA), *T. atroviride* LC52 (e. g. SENTINEL® from Agrimm Technologies Ltd, NZ), *T. atroviride* CNCM I-1237 (e. g. in Esquive WG from Agrauxine S.A., France, e. g. against pruning wound diseases on vine and plant root pathogens), *T. fertile* JM41R (NRRL 50759; e. g. TRICHOPLUS™ from BASF Agricultural Specialities (Pty) Ltd., South Africa), *T. gamsii* ICC 080 (e. g. in TENET WP, REMDIER WP, BIOTEN WP from Isagro N.C., USA, BIO-TAM from AgraQuest, USA), *T. harzianum* T-22 (also called KRL-AG2; ATCC 20847; e. g. PLANTSHIELD® from BioWorks Inc., USA or SabrEx™ from Advanced Biological Marketing Inc., Van Wert, Ohio, USA; BioControl 57, 687-696, 2012), *T. harzianum* TH 35 (e. g. ROOT PRO® from Mycontrol Ltd., Israel), *T. harzianum* T-39 (e. g. TRICHODEX® and TRICHODERMA 2000® from Mycontrol Ltd., Israel and Makhteshim Ltd., Israel), mixture of *T. harzianum* and *T. viride* (e. g. TRICHOPEL from Agrimm Technologies Ltd, NZ), *T. harzianum* ICC012 and *T. viride* ICC080 (e. g. REMEDIER® WP from Isagro Ricerca, Italy), *T. polysporum* and *T. harzianum* (e. g. BINAB® from BINAB Bio-Innovation AB, Sweden), *T. stromaticum* (e. g. TRICOVAB® from C.E.P.L.A.C., Brazil), *T. virens* G1-3 (also called G1-3; ATCC 58678; e.g. QuickRoots™ from TJ Technologies, Watertown, S. Dak., USA; CA 2471555 A1), *T. virens* GL-21 (also called G1-21; U.S. Pat. No. 7,429,477 B2; e. g. SOILGARD® 12G from Certis LLC, USA, EPA Registration Number: 70051-3 and EPA Establishment Number: 067250-IL-001), *T. virens* G-41 (also called 041, #41X or ABM 127; isolated from soil samples taken from *Aphanomyces*-suppressive bean fields in Livingston County, New York; U.S. Pat. No. 4,996,157; e. g. ROOTSHIELD® PLUS from BioWorks, Inc., USA), *T. viride* (e. g. TRIECO® from Ecosense Labs. (India) Pvt. Ltd., Indien, BIO-CURE® F from T. Stanes & Co. Ltd., Indien), *T. viride* TV1 (e. g. *T. viride* TV1 from Agribiotec srl, Italy) and *Ulocladium oudemansii* HRU3 (e. g. in BOTRY-ZEN® from Botry-Zen Ltd, NZ).

Even more preferred biologicals to be used in the process according to the present invention include the following substances and mixtures thereof:

*Bacillus amyloliquefaciens* FZB42 (e. g. in RhizoVital® 42 from AbiTEP GmbH, Berlin, Germany), *B. amyloliquefaciens* IN937a (J. Microbiol. Biotechnol. 17(2), 280-286, 2007; e. g. in BioYield® from Gustafson LLC, TX, USA), *B. amyloliquefaciens* IT-45 (CNCM I 3800) (e. g. Rhizocell C from ITHEC, France), *B. amyloliquefaciens* TJ1000 (also called 1BE; ATCC BAA-390; e.g. QuickRoots™ from TJ Technologies, Watertown, S. Dak., USA; CA 2471555 A1), *B. amyloliquefaciens* ssp. *plantarum* MBI600 (NRRL B-50595, deposited at USDA) (e. g. Integral®, Subtilex® NG from BASF Corp., USA), *B. cereus* CNCM I-1562 (U.S. Pat. No. 6,406,690), *B. firmus* CNCM I-1582 (WO 2009/126473, WO 2009/124707, U.S. Pat. No. 6,406,690; Votivo® from Bayer Crop Science LP, USA), *B. pumilus* GB34 (ATCC 700814; e. g. in YieldShield® from Gustafson LLC, TX, USA), and *Bacillus pumilus* KFP9F (NRRL B-50754) (e. g. in BAC-UP or FUSION-P from BASF Agricultural Specialities (Pty) Ltd., South Africa), *B. pumilus* QST 2808 (NRRL B 30087) (e. g. Sonata® and Ballad® Plus from AgraQuest Inc., USA), *B. subtilis* CX-9060 (Federeal Register 77(7), 1633-1637; Certis U.S.A., L.L.C.), *B. subtilis* GB03 (e. g. Kodiak® or BioYield® from Gustafson, Inc., USA; or Companion® from Growth Products, Ltd., White Plains, N.Y. 10603, USA), *B. subtilis* GB07 (Epic® from Gustafson, Inc., USA), *B. subtilis* QST-713 (NRRL B 21661 in Rhapsody®, Serenade® MAX and Serenade® ASO from AgraQuest Inc., USA), *B. subtilis* var. *amyloliquefaciens* FZB24 (e. g. Taegro® from Novozyme Biologicals, Inc., USA), *B. subtilis* var. *amyloliquefaciens* D747 (FERM BP-8234; KR 100903253; e. g. Double Nickel™ 55 WDG or Double Nickel™ LC from Certis LLC, USA), *Bradyrhizobium* sp. (e. g. Vault® from BASF Corp., USA), *B. japonicum* (e. g. VAULT® from BASF Corp., USA), *Burkholderia* sp. A396 (NRRL B-50319; WO 2013/032693; Marrone Bio Innovations, Inc., USA), *Candida oleophila* I-182 (NRRL Y-18846; e. g. Aspire® from Ecogen Inc., USA, *Coniothyrium minitans* CON/M/91-08 (DSM 9660; e. g. Contans® WG, Intercept® WG from Prophyta Biologischer Pflanzenschutz GmbH, Germany; WO 1996/021358), *Paecilomyces fumosoroseus* FE 9901 (e. g. NO FLY™ from Natural Industries, Inc., USA), *P. lilacinus* 251 (e. g. in BioAct®/MeloCon® from Prophyta, Germany; Crop Protection 27, 352-361, 2008; originally isolated from infected nematode eggs in the Philippines), *P. lilacinus* DSM 15169 (e. g. NEMATA® SC from Live Systems Technology S.A., Colombia), *P. lilacinus* BCP2 (NRRL 50756; e. g. PL GOLD from BASF Agricultural Specialities (Pty) Ltd., South Africa), mixture of *Paenibacillus alvei* NAS6G6 (NRRL B-50755) and *Bacillus pumilus* (e.g. BAC-UP from BASF Agricultural Specialities (Pty) Ltd., South Africa), *Pasteuria* sp. ATCC PTA-9643 (WO 2010/085795), *P. nishizawae* Pn1 (e.g. CLARIVA PN from Syngenta Crop Protection, LLC, Greenborom; C, USA), *Pasteuria* sp. ATCC SD-5832 (WO 2012/064527), *P. nishizawae* (WO 2010/80169), *P. penetrans* (U.S. Pat. No. 5,248,500), *P. ramose* (WO 2010/80619), *P. thornea* (WO 2010/80169), *P. usgae* (WO 2010/80169), *Penicillium bilaiae* (e. g. Jump Start® from Novozymes Biologicals BioAg Group, Canada, originally isolated from soil in southern Alberta; Fertilizer Res. 39, 97-103, 1994), *Pseudomonas* sp. DSM 13134 (WO 2001/40441, e. g. in PRORADIX from Sourcon Padena GmbH & Co. KG, Hechinger Str. 262, 72072 Tübingen, Germany), *P. chloraphis* MA 342 (e. g. in CERALL or CEDEMON from BioAgri AB, Uppsala, Sweden), *P. fluorescens* CL 145A (e. g. in ZEQUANOX from Marrone BioInnovations, Davis, Calif., USA; J. Invertebr. Pathol. 113(1):104-14, 2013), *Rhizobium leguminosarum* bv. *phaseoli* (e. g. RHIZO-STICK from BASF Corp., USA), R. l. bv. *trifolii* RP113-7 (e. g. DORMAL from BASF Corp., USA; Appl. Environ. Microbiol. 44(5), 1096-1101), R. l. bv. *viciae* P1NP3Cst (also referred to as 1435; New Phytol. 179(1), 224-235, 2008; e. g. in NODULATOR PL Peat Granule from BASF Corp., USA; or in NODULATOR XL PL from BASF Agricultural Specialties Ltd., Canada), R. l. bv. *viciae* SU303 (e. g. NODULAID Group E from BASF Agricultural Specialties Pty Ltd, Australia), R. l. bv. *viciae* WSM1455 (e. g. NODULAID Group F from BASF Agricultural Specialties Pty Ltd, Australia), *Sinorhizobium meliloti* MSDJ0848 (INRA, France) also referred to as strain 2011 or RCR2011 (Mol. Gen. Genomics 272, 1-17, 2004; e. g. DORMAL ALFALFA from BASF Corp., USA; NITRAGIN® Gold from Novozymes Biologicals BioAg Group, Canada), *Trichoderma asperellum* SKT-1 (e. g. ECO-HOPE® from Kumiai Chemical Industry Co., Ltd., Japan), *T. asperellum* ICC 012 (e. g. in TENET WP, REMDIER WP, BIOTEN WP from Isagro N.C., USA, BIO-TAM from AgraQuest, USA), *T. atroviride* LC52 (e. g. SENTINEL® from Agrimm Technologies Ltd, NZ), *T. atroviride* CNCM I-1237 (e. g. in Esquive WG from Agrauxine S.A., France, e. g. against pruning wound diseases on vine and plant root pathogens), *T. fertile* JM41R (NRRL 50759; e. g. TRICHOPLUS™ from BASF Agricultural Specialities (Pty) Ltd., South Africa), *T. gamsii* ICC 080 (e. g. in TENET WP, REMDIER WP, BIOTEN WP from Isagro N.C., USA, BIO-TAM from AgraQuest, USA), *T. harzianum* T-22 (also called KRL-AG2; ATCC 20847; e. g. PLANTSHIELD® from BioWorks Inc., USA or SabrEx™ from Advanced Biological Marketing Inc., Van Wert, Ohio, USA; BioControl 57, 687-696, 2012), *T. harzianum* TH 35 (e. g. ROOT PRO® from Mycontrol Ltd., Israel), *T. harzianum* T-39 (e. g. TRICHODEX® and *TRICHODERMA* 2000® from Mycontrol Ltd., Israel and Makhteshim Ltd., Israel), mixture of *T. harzianum* and *T. viride* (e. g. TRICHOPEL from Agrimm Technologies Ltd, NZ), *T. harzianum* ICC012 and *T. viride* ICC080 (e. g. REMEDIER® WP from Isagro Ricerca, Italy), *T. polysporum* and *T. harzianum* (e. g. BINAB® from BINAB Bio-Innovation AB, Sweden), *T. stromaticum* (e. g. TRICOVAB® from C.E.P.L.A.C., Brazil), *T. virens* G1-3 (also called G1-3; ATCC 58678; e.g. QuickRoots™ from TJ Technologies, Watertown, S. Dak., USA; CA 2471555 A1), *T. virens* GL-21 (also called G1-21; U.S. Pat. No. 7,429,477 B2; e. g. SOILGARD® 12G from Certis LLC, USA, EPA Registration Number: 70051-3 and EPA Establishment Number: 067250-IL-001), *T. virens* G-41 (also called 041, #41X or ABM 127; isolated from soil samples taken from *Aphanomyces*-suppressive bean fields in Livingston County, New York; U.S. Pat. No. 4,996,157; e. g. ROOTSHIELD® PLUS from BioWorks, Inc., USA), *T. viride* (e. g. TRIECO® from Ecosense Labs. (India) Pvt. Ltd., Indien, BIO-CURE® F from T. Stanes & Co. Ltd., Indien), *T. viride* TV1 (e. g. *T. viride* TV1 from Agribiotec srl, Italy).

The most preferred biologicals to be used in the process according to the present invention include the following substances and mixtures thereof:

*Bacillus amyloliquefaciens* FZB42 (e. g. in RhizoVital® 42 from AbiTEP GmbH, Berlin, Germany), *B. amyloliquefaciens* IN937a (J. Microbiol. Biotechnol. 17(2), 280-286, 2007; e. g. in BioYield® from Gustafson LLC, TX, USA), *B. amyloliquefaciens* IT-45 (CNCM I 3800) (e. g. Rhizocell C from ITHEC, France), *B. amyloliquefaciens* TJ1000 (also called 1BE; ATCC BAA-390; e.g. QuickRoots™ from TJ Technologies, Watertown, S. Dak., USA; CA 2471555 A1), *B. amyloliquefaciens* ssp. *plantarum* MBI600 (NRRL B-50595, deposited at USDA) (e. g. Integral®, Subtilex® NG from BASF Corp., USA), *B. cereus* CNCM I-1562 (U.S. Pat. No. 6,406,690), *B. firmus* CNCM I-1582 (WO 2009/126473, WO 2009/124707, U.S. Pat. No. 6,406,690; Votivo® from Bayer Crop Science LP, USA),

*Bacillus pumilus* KFP9F (NRRL B-50754) (e. g. in BAC-UP or FUSION-P from BASF Agricultural Specialities (Pty) Ltd., South Africa), *B. pumilus* QST 2808 (NRRL B 30087) (e. g. Sonata® and Ballad® Plus from AgraQuest Inc., USA), *B. japonicum* (e. g. VAULT® from BASF Corp., USA), *Coniothyrium minitans* CON/M/91-08 (DSM 9660; e. g. Contans® WG, Intercept® WG from Prophyta Biologischer Pflanzenschutz GmbH, Germany; WO 1996/021358), *P. nishizawae* Pn1 (e.g. CLARIVA PN from Syngenta Crop Protection, LLC, Greenborom; C, USA), *Penicillium bilaiae* (e. g. Jump Start® from Novozymes Biologicals BioAg Group, Canada, originally isolated from soil in southern Alberta; Fertilizer Res. 39, 97-103, 1994), *P. fluorescens* CL 145A (e. g. in ZEQUANOX from Marrone BioInnovations, Davis, Calif., USA; J. Invertebr. Pathol. 113(1):104-14, 2013), *Rhizobium leguminosarum* bv. *phaseoli* (e. g. RHIZO-STICK from BASF Corp., USA), R. l. bv. *trifolii* RP113-7 (e. g. DORMAL from BASF Corp., USA; Appl. Environ. Microbiol. 44(5), 1096-1101), R. l. bv. *viciae* P1NP3Cst (also referred to as 1435; New Phytol. 179(1), 224-235, 2008; e. g. in NODULATOR PL Peat Granule from BASF Corp., USA; or in NODULATOR XL PL from BASF Agricultural Specialties Ltd., Canada), R. l. bv. *viciae* SU303 (e. g. NODULAID Group E from BASF Agricultural Specialties Pty Ltd, Australia), R. l. bv. *viciae* WSM1455 (e. g. NODULAID Group F from BASF Agricultural Specialties Pty Ltd, Australia), *Sinorhizobium meliloti* MSDJ0848 (INRA, France) also referred to as strain 2011 or RCR2011 (Mol. Gen. Genomics 272, 1-17, 2004; e. g. DORMAL ALFALFA from BASF Corp., USA; NITRAGIN® Gold from Novozymes Biologicals BioAg Group, Canada), *T. fertile* JM41R (NRRL 50759; e. g. TRICHOPLUS™ from BASF Agricultural Specialities (Pty) Ltd., South Africa).

In another preferred embodiment, the biological to be used in the process according to the present invention is a biochemical compound selected from the group consisting of geraniol, cuminaldehyde, vanillin, borneol, menthol, anethole, terpineol, limonene, citronellol, eugenol, isoeugenol, linalool, phenylethyl alcohol, most preferably geraniol. These biochemical compounds can act as fragrances.

In another preferred embodiment, the biological 1 to be used in the process according to the present invention is *Bacillus subtilis*, most preferably *B. subtilis* strain FB 17.

The biological is present in the functional coating of the particulate material in an amount of $1 \times 10^2$ to $1 \times 10^8$ CFU/gram, preferably $1 \times 10^3$ to $1 \times 10^7$ CFU/gram, and even more preferably $5 \times 10^3$ to $5 \times 10^5$ CFU/gram based on the particulate material. In case the biological is a non-microbial, biochemical compound, the biological is present in the functional coating of the particulate material in an amount of 0.001 to 1.0% by weight, preferably 0.005 to 0.5% by weight, and even more preferably 0.01 to 0.1% by weight based on the particulate material.

Preferred nutrients to be used in the process according to the present invention include the following substances and mixtures thereof:

Alpha-tocopherol, trehalose, glutamate, potassium sorbate, various sugars like glucose, sucrose, lactose and maltodextrine (see H. D. Burges: Formulation of Micobial Biopesticides, Springer, 1998).

Preferred surfactants and/or wetting agents to be used in the process according to the present invention include the following substances and mixtures thereof:

Alkali metal, alkaline earth metal and ammonium salts of aromatic sulfonic acids, such as ligninsoulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany), and fatty acids, alkylsulfonates, alkyl-arylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, tristearyl-phenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e. g. methylcellulose), hydrophobically modified starches, polyvinyl alcohols (Mowiol® types, Clariant, Switzerland), polycarboxylates (Sokolan® types, BASF, Germany), polyalkoxylates, polyvinyl-amines (Lupasol® types, BASF, Germany), polyvinylpyrrolidone and the copolymers thereof.

The nutrients, surfactants and/or wetting agents are present in the functional coating of the particulate material in an amount of 0.001 to 1.0% by weight, preferably 0.005 to 0.5% by weight, and even more preferably 0.01 to 0.1% by weight based on the particulate material.

The functional additive or (coating) material according to the present invention may be optionally combined with other materials, like colorants. A colorant is a material containing a pigment or dye that is applied to change the color of the particulate material, preferably mulch. The colorant does not affect the functionalized treatment provided to the particulate material modified by the process according to the present invention. Additional optional materials may include aluminium silicate (Screen™ Duo from Certis LLC, USA) and/or potassium silicate (e. g. Sil-MATRIX™ from Certis LLC, USA).

A carrier may be added to the flow of the coating material. In a preferred process, the carrier is in liquid form, like water or glycerine or mixtures thereof. An especially preferred liquid carrier is water. A dry carrier is less preferred.

The carrier is preferably supplied separate from the coating material(s) within the storage means. A carrier material is typically mixed with the coating material to form a coating mixture. Generally, a coating mixture is defined as being a mixture of two or more materials, which may be selected from a group comprising functional additives and carriers.

Preferred dry carriers include clay, kaolin clay, sodium bicarbonate, and the like. In a further embodiment of the present invention, the carrier can be a composition of a polysiloxane, at least one polyalkylene glycol, and a co-product comprised of monopropylene glycol and a propylene oxide according to WO 2010/104912 A1. In another alternative of the present invention, the composition contains no carrier.

The storage means 16, 18 are connected with pumping means 24 for directing the coating material (etc.) to a coating delivery system (or application system, discussed further below) within the mixer 14. Any desired form of pump may be provided, with peristaltic pumps being one preferred form for delivering the coating materials. For the high pressure carrier flow, one pump example is a multi-stage pressure pump. Again, other pump forms may be utilized. A controller 20 is shown adjacent the pumping means 24 and the mixer 14. The pumping means or controller may be mounted on the frame of the mixer or otherwise located. The controller 20 may take any number of forms and be provided with various communication capabilities. The controller may perform one or more functions, such as remote operational monitoring and control, data extract, software update, general maintenance, etc. One possible example of a controller/control panel is an Allen Bradley Micrologix 1400 PLC sold by Rockwell Automation of Milwaukee, Wis.

A discharge mechanism 22 is provided at a discharge end of the mixer 14. The discharge mechanism 22 is shown as a belt conveyor and is intended to transport the coated particulate material away from the mixer 10 and direct it for further processing. Other processing steps, packaging operations or storage methods (not shown) may be utilized or added, as desired. A drive motor 26 is mounted on the mixer 14 for rotation of an agitating conveyor (discussed below) within the mixer 14. A hydraulic drive motor 28 is also provided as part of the feed means 12.

The feed means 12 comprises a hopper 32 having a floor forming a conveyor 30 for moving the particulate material deposited within the hopper 32 towards a discharge. The hopper 32 is connected with an inlet 42 for the mixer 14. Two baffles 36A, 36B are provided at the discharge end of the hopper 32. A web 35 formed from chains (or similar structures) extends across the open top of the hopper 32. The web 35 serves to disturb the particulate 34A deposited in the hopper 32 and assists in leveling the particulate 34A as it is moved by the conveyor 30 towards discharge.

Figure 2:
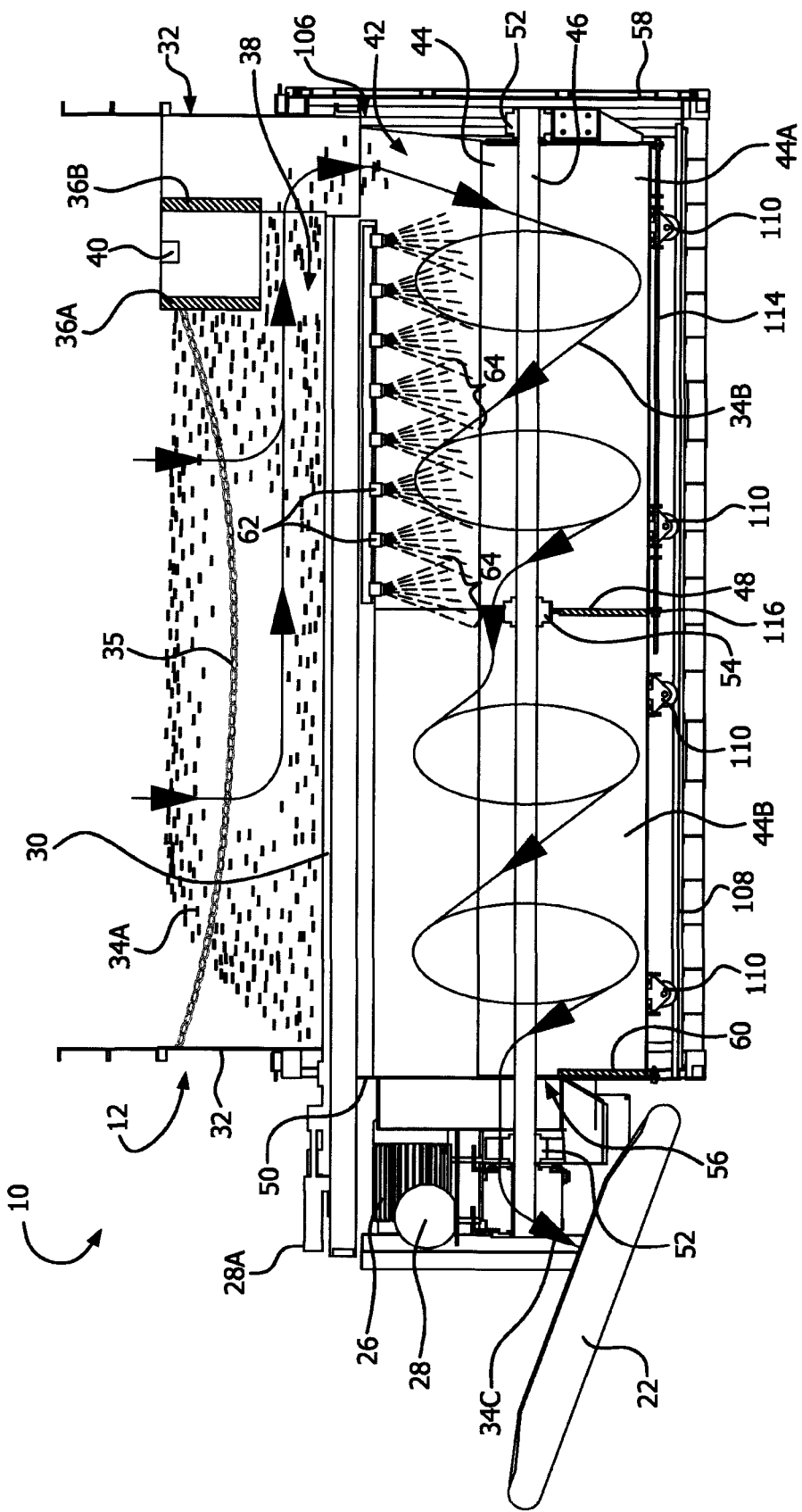
FIG. 2 shows a cross sectional view of the apparatus with certain material flow patterns illustrated within a feed conveyor portion and a mixer portion thereof.

In FIG. 2 there is shown the general flow of the particulate material 34A through the apparatus 10. The feed means 12 includes a conveyor 30 forming the floor for the hopper 32. Particulate feed material 34A is deposited into the hopper 32 and sits on top of the conveyor 30. The conveyor 30 moves the particulate feed 34A towards the baffles 36A, 36B (to the right in FIG. 2). Although two baffles are shown, one or more baffles may be provided. The baffles 36A, 36B extend across the hopper 32 and define a control gate 38 for the particulate flow. In the embodiment shown, the first baffle 36A defines the maximum height of the flow of particulate material through the gate 38. However, the baffles may be set at a variety of heights, with the flow control acting in sequence (or otherwise) in defining the height of the particulate flow. The chain web 35 engages the particulate feed 34A and agitates the material to break-up or otherwise settle the bulk pile.

One or more sensors 40 (two being shown) are provided between the baffles 36A, 36B to measure the height of the feed material 34A passing under the baffle 36A and through the gate 38. The signals from the sensors 40 are sent to the controller 20 and are used to calculate the cubic meters per minute (m³/min) feed rate into the mixer 14. The overall volumetric flow is a function of the incremental rate of the movement by the conveyor 30 multiplied by the width of the hopper (which is typically fixed) and the height of the particulate passing under the baffle 34A. For a relatively full hopper 32, the particulate 34A will have a maximum height defined by the bottom edge of the baffle 36A. The sensors 40 are contemplated to create a more accurate measurement of the height of the particulate 34A, particularly where the flow passes freely under the baffle 36A. In other embodiments (not shown), sensors may instead, or additionally, be positioned at or adjacent the exit of the mixer 14 for determining the flow rate of particulate material exiting the mixer.

After moving through the gate 38, the particulate feed 34A passes under the second baffle 36B (if provided) and falls into a mixer inlet 42 at the end of the conveyor 30. The mixer inlet 42 is connected with the mixer 14, having a defined mixing chamber therein. A trough 44 defines the base of the mixing chamber and extends along the longitudinal length of the mixer 14. A shaft 46 is provided for rotation of an agitating conveyor (discussed below). The trough 44 is divided into two sections 44A, 44B by a weir plate 48. The shaft 46 is mounted in the mixer 14 and is supported at each end by a bearing 52. A central support bearing 54 is also shown as mounted on top of the weir plate 48. The drive motor 26 is connected to the shaft 46 at the discharge end 50 of the mixer 14. A discharge opening 56 is provided in the mixer housing 58 at the discharge end 50 of the mixer 14. A discharge weir 60 is positioned at the end of the trough 44, adjacent the discharge opening 56.

A plurality of nozzles 62 are provided above the trough 44 and are shown to be positioned in the initial portion of the mixing chamber. The nozzles 62 are preferably aligned axially along the mixing chamber with a series of plenums and valves (discussed below) directing the constituent parts of a coating mixture to the nozzles 62. Other nozzle positions and alignments are possible. The nozzles 62 preferably convert the coating or coating mixture to an atomized spray 64. Further, the atomization of the coating or coating mixture is preferably created without the addition of a pressurized gas. The nozzles 62 direct the atomized spray 64 towards the mixing particulate 34B within the mixing chamber.

As generally illustrated by the arrows in FIG. 2, an agitator mixes the particulate 34B within the trough 44 while conveying it towards a discharge end 50 of the mixing chamber. The weir plate 48 serves to control the flow of mixing particulate 34B within the trough 44. The position of the weir plate may be varied as desired and other weir plates may be added. The nozzles 62 are positioned above the first trough portion 44A. A discharge weir 60 also serves to control flow of particulate 34B, generally increasing residence time for the particulate 34B within the mixing chamber. The coated particulate 34C is ultimately directed through the discharge opening 56 by the agitator. The discharge particulate 34C passes through the discharge opening 56 and onto the discharge mechanism 22, which is shown to be a belt conveyor.

Figure 3:
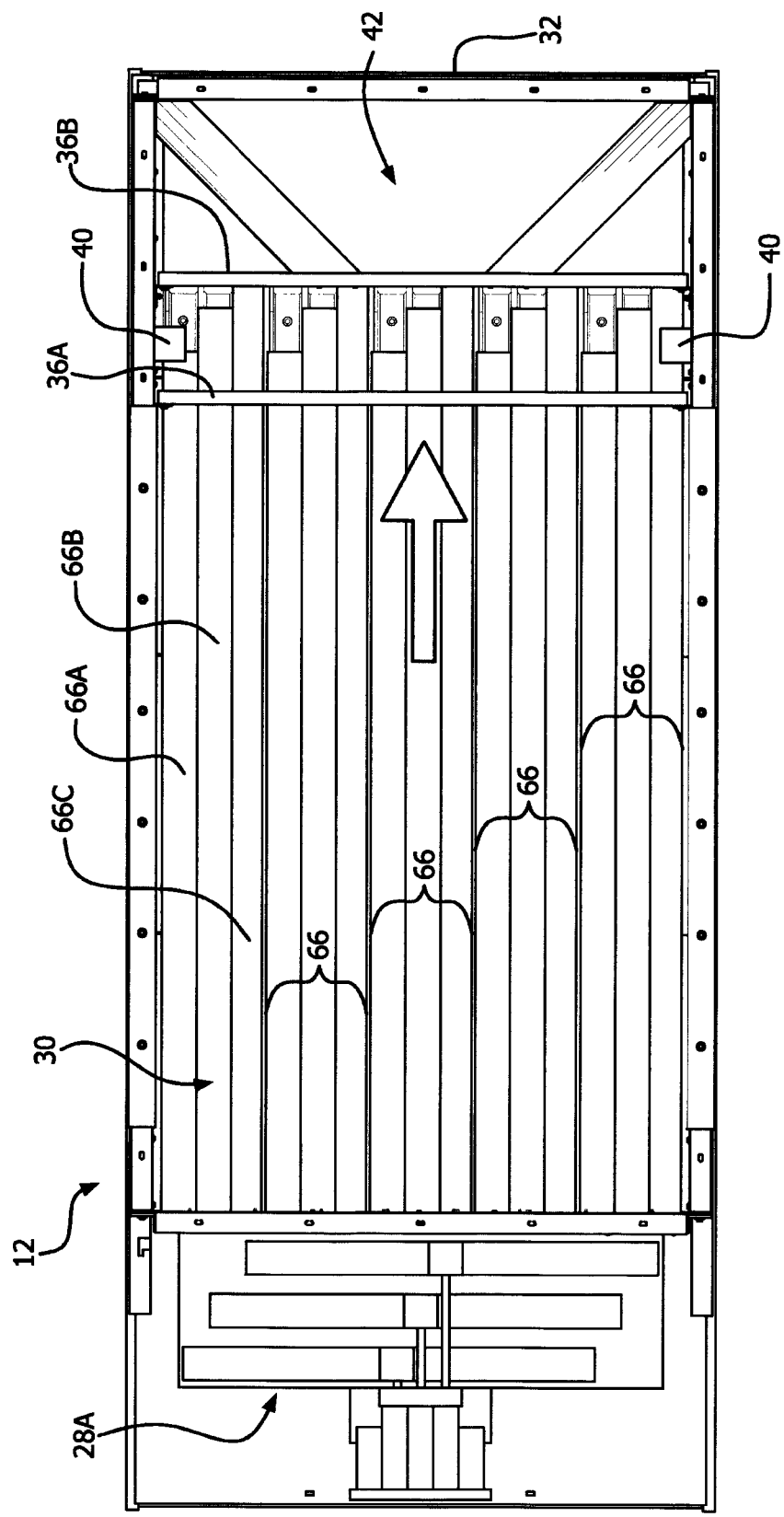
FIG. 3 shows a top plan view of a feed conveyor portion of the apparatus.
Figure 4:
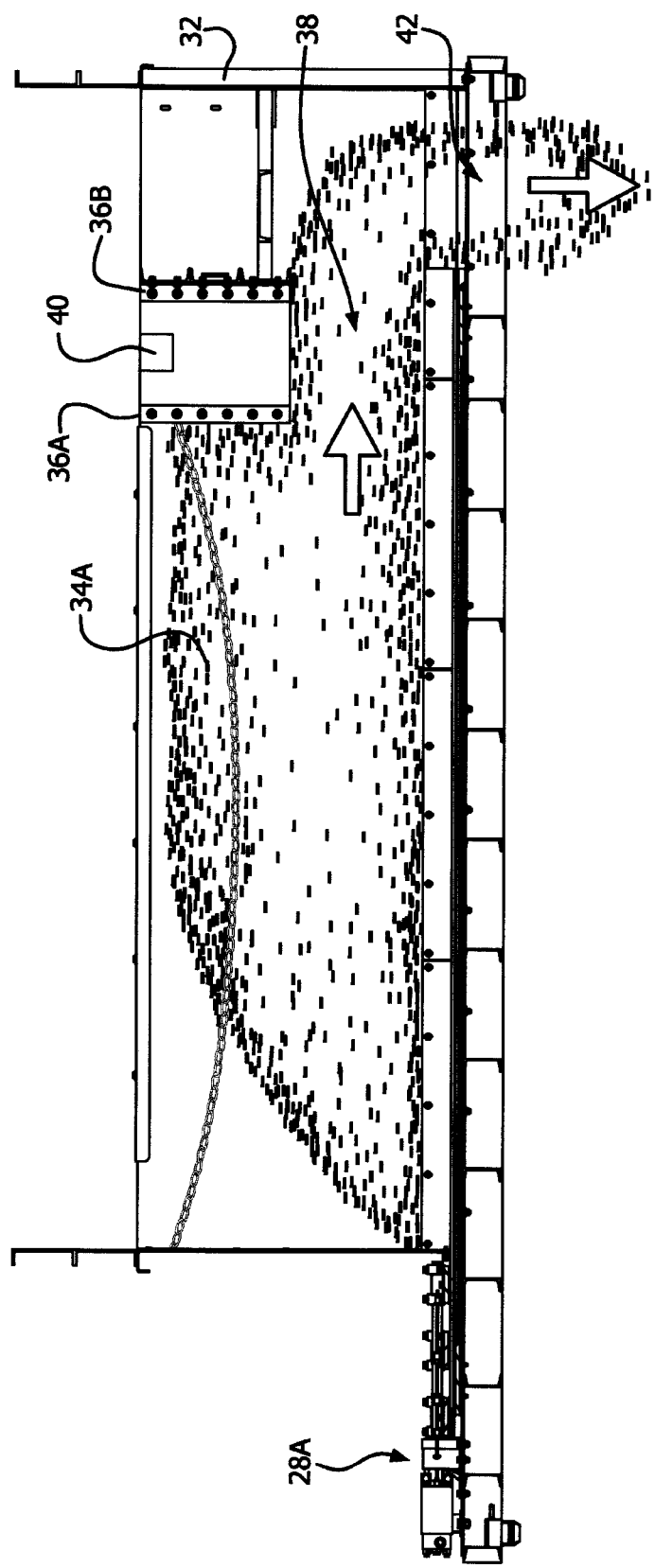
FIG. 4 shows a cross sectional view of the feed conveyor of FIG. 3 with feed material shown as being conveyed towards an inlet of the mixer portion of the apparatus.

The feed means 12 is shown in more detail in FIGS. 3 and 4. The particulate feed 34A is initially directed into the hopper 32 by any desired method, including front end loader, conveyor, etc. The feed 34A may preferably include any number of particulate materials, such as wood mulch, chipped or crumb rubber or plastic materials. The feed material 34A is contemplated to be stored in bulk prior to introduction into the apparatus 10. The particulate feed may also be provided to the hopper by other means, such a being fed directly from a grinder (not shown), used to convert unprocessed material to a particulate form. The conveyor 30 is preferably in the form of a slat conveyor having a push-pull type operation. Slats 66 are provided longitudinally along the conveying surface and are typically operated in sets of three 66A, 66B and 66C. The slats 66A, 66B, 66C move together toward the discharge end to incrementally convey the particulate material 34A. The slats 66 return to the initial starting position in sequence. Hence, during reset of the conveyor, only one slat in each group of three is returning at a time, with two slats remaining fixed. The friction of the load on the two non-moving slats in the set keeps the load from moving backwards along with the one returning slat. Once the three slats have all returned to their incremental starting position, the conveying cycle is repeated. The slat conveyor 30 is contemplated to be powered by a hydraulic motor 28 (FIGS. 1 and 2). The motor 28 is connected to a slat actuator 28A, which is generally illustrated adjacent the hopper 32 at the opposite end from the gate 38 and the conveyor discharge. A slat conveyor of the type described may be provided from any number of sources, including systems produced by Hallco Industries, Inc. of Tillamook, Oreg. and Keith Manufacturing Co. of Madras, Oreg. The hydraulic drive 28 may have a variable speed control for adjusting the rate of feed by the conveyor 30. The conveying speed may be adjusted through the controller 20 or otherwise. The stroke length per cycle of the slats may be adjustable to also assist in controlling the particulate flow rate.

The slat conveyor 30 directs the feed material 34A towards the control gate 38 formed below the baffle 36A. The bottom edge of the baffle 36A defines the height of the gate 38, with the side walls of the hopper 32 and the conveyor slats 66 further defining the dimensions of the gate 38. The chain web 35 extends across the hopper 32 and is contemplated to be at least partially covered in normal operation by the accumulated particulate feed material 34A. As shown, the chain web is connected at various positions within the hopper 32 and to the baffle 36A. As the particulate feed 34A is moved by the conveyor 30 towards the gate 38, the pile of particulate 34A is subject to agitation and shearing forces, serving to break up and level the pile as it approaches the baffle 36A.

The position of the baffle 36A (and baffle 36B) may be adjusted to set the maximum volume of feed material 34A passing through the gate 38 during operation of the conveyor 30. The width of the gate 38 is contemplated to be fixed. The sensors 40 are positioned at the gate 38 to assist in the volumetric flow measurement for the feed material 34A passing through the gate 38 and into the inlet 42 of the mixer 14. The sensors 40 are contemplated to provide a more accurate height measurement; for example, to adjust for a particulate flow having a height less than the bottom edge of the baffle 34A. One possible sensor-type may be an ultrasonic sensor, such as those sold by Pepperl+Fuchs of Twinsburg, Ohio. The conveyor 30 and sensor 40 are contemplated to receive signals from and send signals to the controller 20. The signals are used by the controller 20 to operate the apparatus 10 and the controller 20 may be programmed to adjust the conveyor speed. Stroke length may be manually adjusted.

Figure 5:
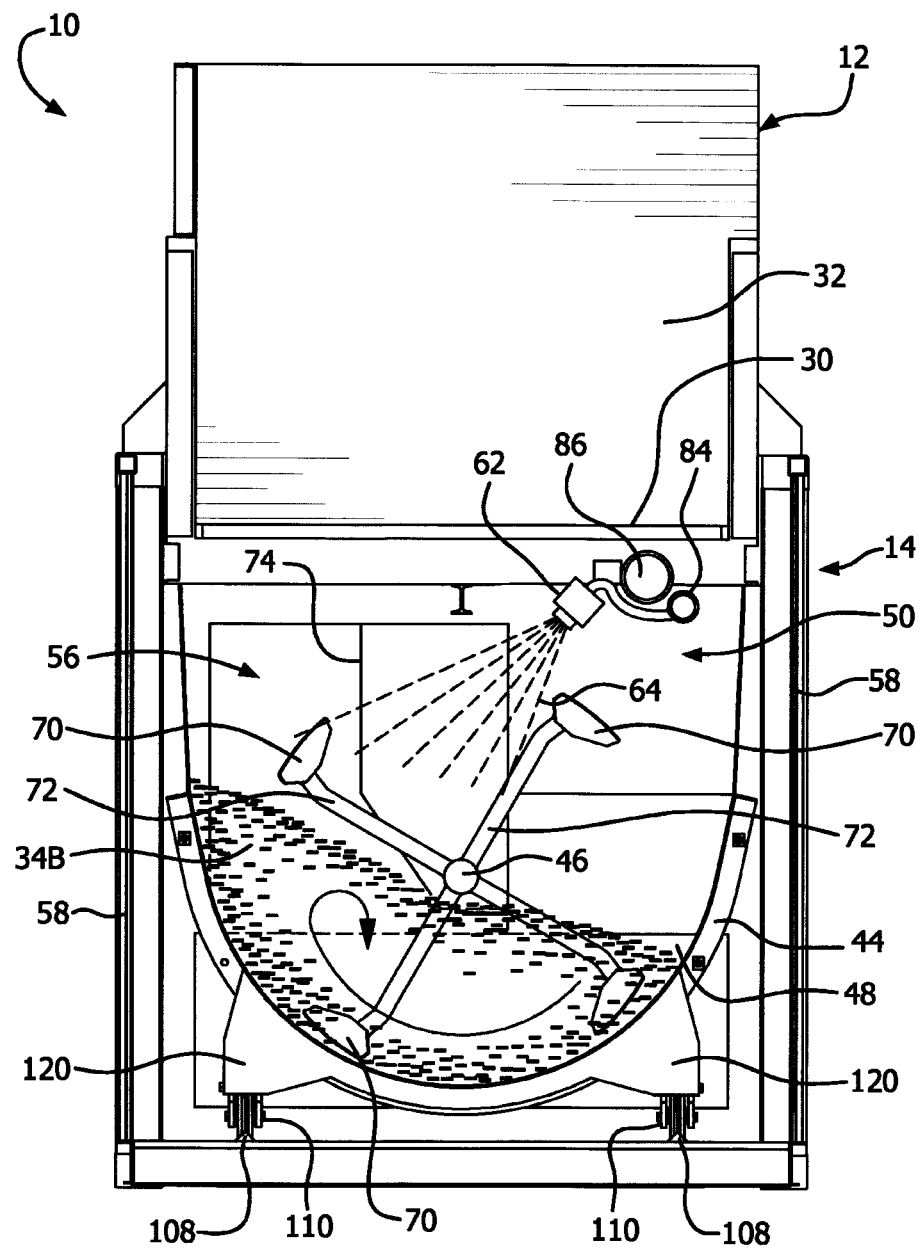
FIG. 5 shows a cross sectional view in the direction of the discharge end of the mixer portion of the apparatus.
Figure 8:
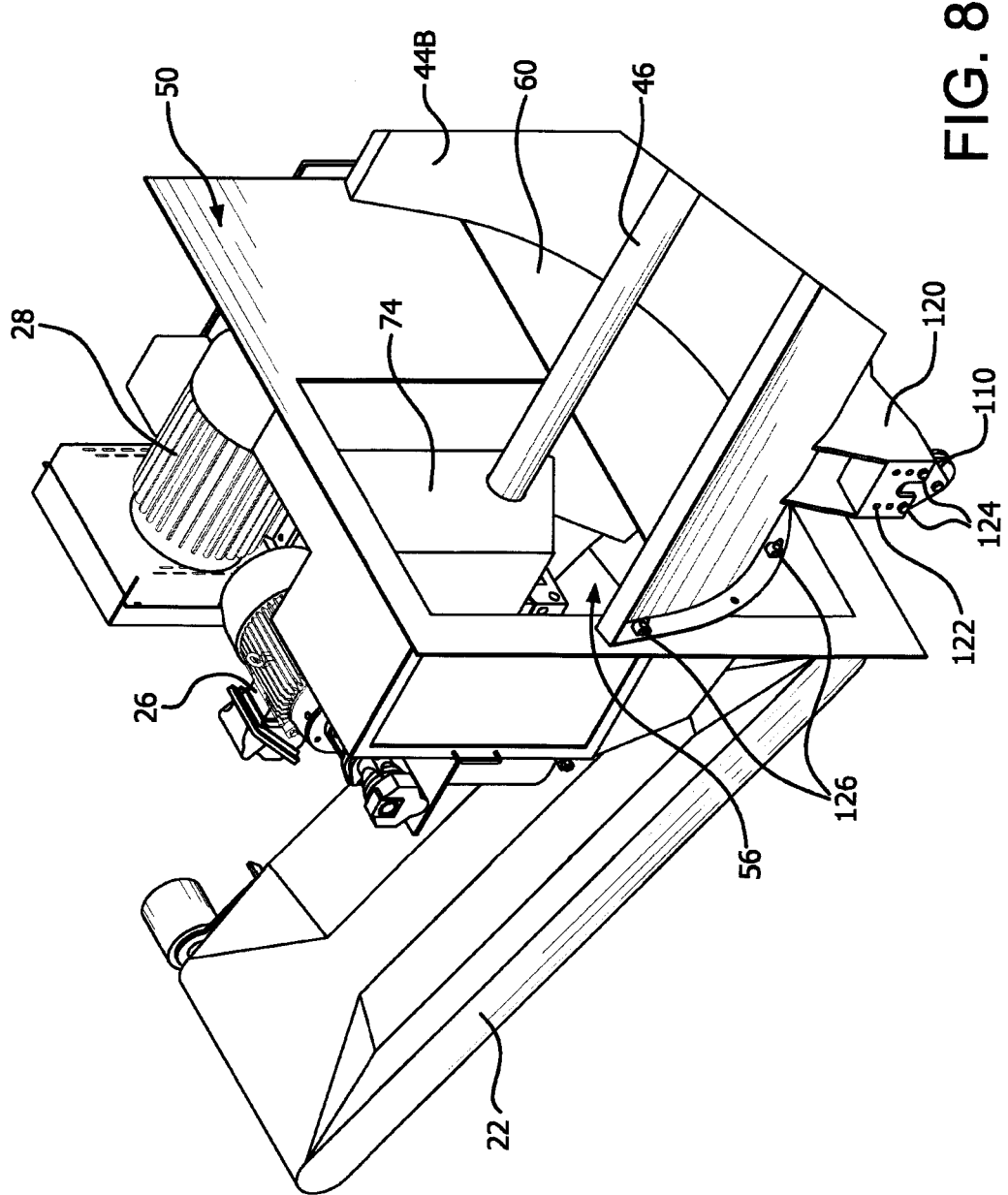
FIG. 8 shows an isometric view of a discharge end of the mixer portion of the apparatus.

In FIG. 5, the interior of the mixer 14 is shown in the direction of the discharge end 50 and discharge opening 56. The trough 44 forms the base of the mixing chamber and retains the mixing particulate material 34B during agitation and conveyance by paddle blades 70. The paddles 70 are supported on arms 72 that project outwardly from the shaft 46. A housing 74 is provided at the end of the shaft 46 to retain the bearings (52) and the connection to the drive motor (26). The housing 74 is positioned adjacent the discharge opening 56 at the discharge end 50 of the mixer 14, as shown in FIG. 8. The trough 44 is retained within the plurality of walls that form the housing 58. The trough 44 and surrounding housing define the mixing chamber. One of the spray nozzles 62 is shown positioned above the trough 44 and above the mixing paddles 70.

The spray 64 from the nozzles 62 is directed towards the particulate material 34B as it is lifted by the paddles 70 within the trough 44. The lifting and mixing action of the paddle blades 70 is illustrated by the arrow in FIG. 5. The typical profile of the mixing particulate 34B within the trough 44 is shown as being relatively higher in the forward direction of the agitator, which is contemplated to be rotating clockwise in FIG. 5. The nozzles 62 are preferably in an offset position relative to the shaft 46. The spray 64 extends over the shaft 46 and towards the high side of the mixing particulate 34B. This position of the nozzles 62 serves to lengthen the spray 64 from nozzle 62 to particulate contact and in effect equalizes and/or maximizes the spread of spray.

The center weir plate 48 is positioned within the trough 44 between the two trough sections 44A and 44B. The weir plate 48 serves to form an impediment to continuous flow through the trough 44 and thus increases retention of the mixing particulate 34B within the mixing chamber. The mixing particulate 34B will accumulate at the upstream side of the plate 48, prior to being lifted over the top edge of the weir 48 by the adjacent paddle blade(s) 70. As shown in FIG. 2, the general flow of the mixing particulate 34B in the mixing chamber is in the direction of the discharge opening 56. The paddle blades 70 on the agitator are normally angled to direct the material flow towards discharge. The paddle blades 70 are contemplated to lift the mixing particulate 34B over the center weir 48, as well as lift the material over the discharge weir 60 at the end of the trough 44. A number of paddle blades may be provided at alternative angles to create a counter flow of the particulate 34B at various positions along the longitudinal length of the trough 44. In one example, for every three sets of forward directed mixing paddles, one set of counter flow paddles may be provided. The counter flow paddles serve to reverse a portion of the mixing particulate 34B, increasing residence time within the mixing chamber and generally increasing the amount of agitation of the particulate with the coating material(s).

In one preferred construction, a total of sixteen arm positions may be provided along the shaft 46. A greater or lesser number of arm positions may be provided. It is further contemplated that the longitudinal position of the paddle arms 72 on the shaft 46 may be adjusted during set-up of the apparatus 10. For example, there may be provided a twenty centimeter adjustment along the shaft 46 for each paddle set. This adjustment of the paddle position may be used to affect material build-up within the mixing chamber, such as adjacent the upstream side of the weir plats 48, 60. The paddle blades 70 moving through this increased quantity of material may result in an increase in the overall load on the drive motor 26. Moving the arms 72, for example, a short distance away from the upstream side of weir plates (48, 60) may serve to reduce or eliminate unnecessary load while not significantly affecting agitation or conveyance by the agitator. Variation in the angular orientation of the paddle blades 70 within adjacent paddle sets may further serve to positively regulate the mixing and flow of the particulate 34B within the mixing chamber. Preferably, the direction of the paddle blades 70 and position of the paddle arms 72 on the shaft 46 creates a generally uniform flow and depth of material within the trough 44.

The controller 20 may further adjust the mixer operation by measurement of motor load. An increase in load on the agitator motor 26 may result form an increase in the overall amount of mixing particulate 34B within the trough 44. The controller 20 may adjust the feed rate of the conveyor 30 to return the particulate flow to a preferred range and motor load. An adjustment of the coating flow may also accompany the adjustment of the particulate feed rate into the mixing chamber. Adjustments to the rotational speed of the agitator may also be accomplished, although it is the preferred that such adjustments do not occur during the operation of the apparatus 10.

Figure 6A:
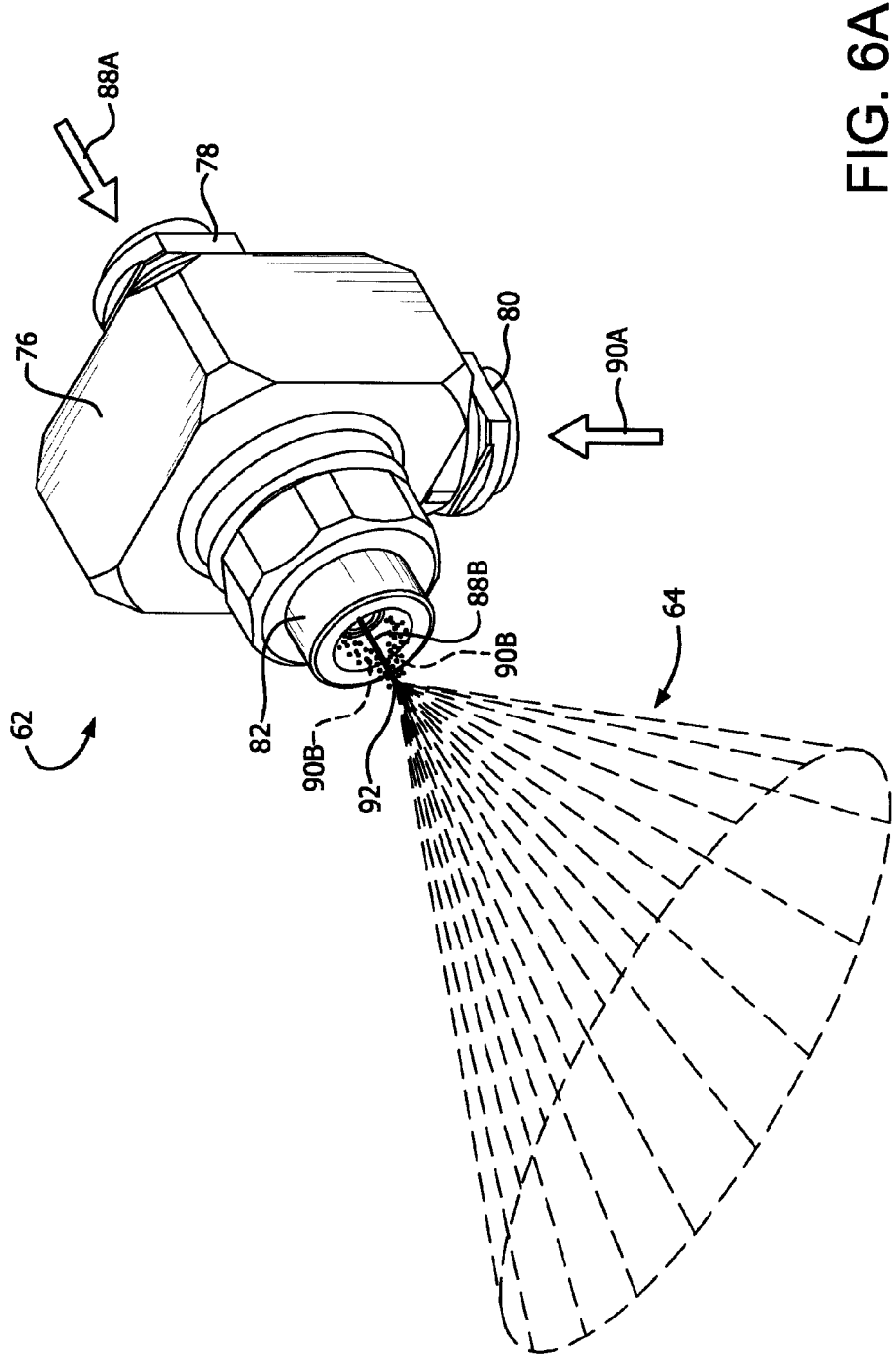
FIG. 6A shows an enlarged, isometric view of a nozzle structure for use in the mixer portion of the apparatus.
Figure 6B:
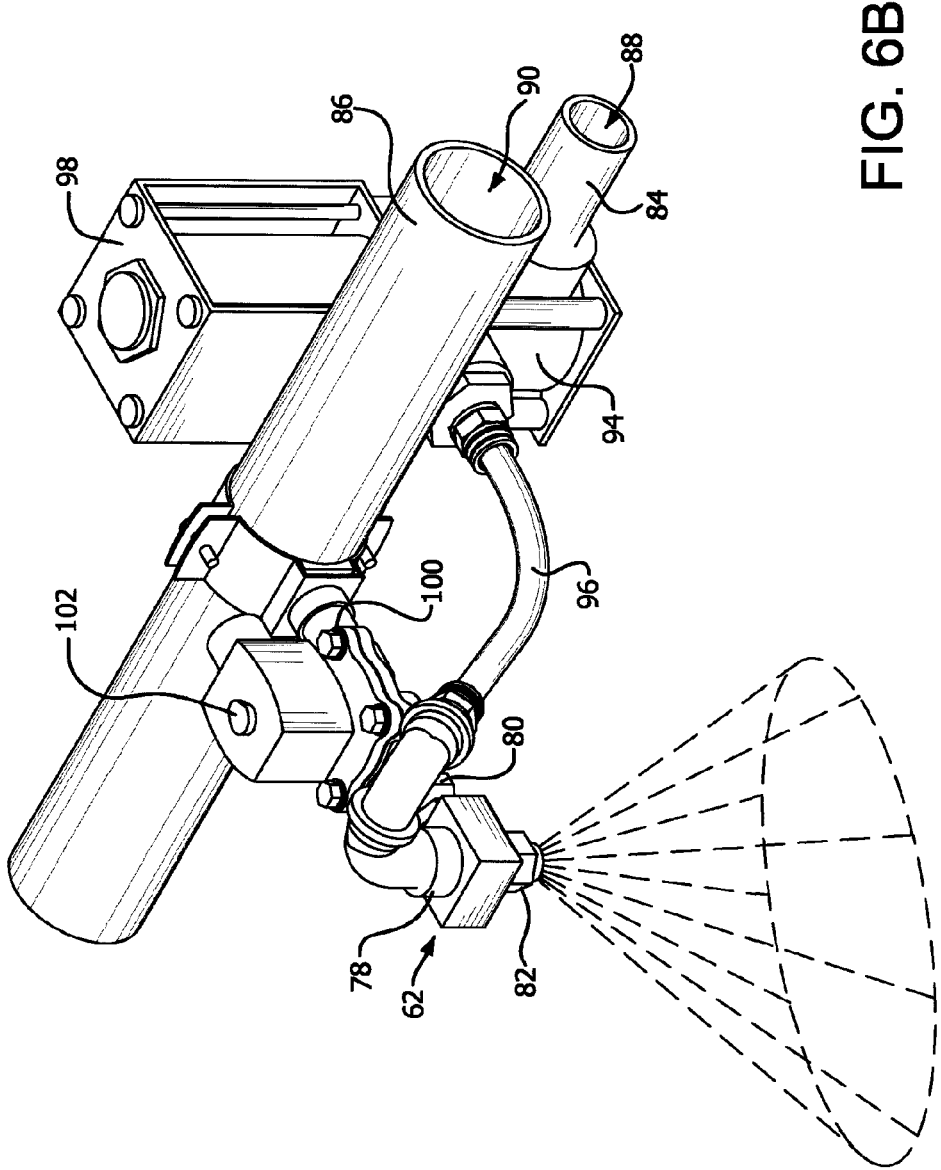
FIG. 6B shows a partial, isometric view of the valve and control structures for the nozzle of the type shown in FIG. 6A.

Details of the spray nozzles 62 and the spray pattern 64 within the mixing chamber are shown in FIGS. 6A, 6B and 7. In FIG. 6A, the construction of an external mix, atomization type nozzle 62 is shown. The nozzle 62 includes a body 76 having two inlet connections 78, 80 and a single discharge orifice 82. One inlet 78 is contemplated to be connected to a plenum or manifold 84 (FIG. 6B) for feed of the coating or coating mixture received from the storage means 16 and/or 18(FIG. 1). The second inlet 80 is connected to a second plenum or manifold 86 (FIG. 6B), preferably for feed of a carrier material, which is a high pressure carrier flow. For example, in one embodiment the carrier flow is at a pressure of about 100 psi to about 150 psi. One preferred carrier material is an aqueous liquid, and more preferably water. The nozzle body 76 is constructed to direct these separate flows to the outlet orifice 82, with the orifice 82 combining the two to form the spray pattern 64. As shown in FIG. 6A, the coating flow 88A directed into the inlet 78 forms a concentrated central stream 88B within the orifice 82. The carrier flow 90A is input through the second inlet 80 of the body 76 and forms an outer outlet stream 90B. The carrier outlet stream 90B is channeled along the outer periphery of the orifice 82. The stream 90B impinges on stream 88B at a position 92 downstream from the orifice 82. The two streams 88B, 90B mix together at the impingement position and form the spray pattern 64. As shown in FIGS. 2, 5 and 7 the spray 64 is directed towards the mixing particulate 34B in the trough 44.

In FIG. 6B, there is shown the various feed plenums or manifolds 84 and 86 that generally direct flow 88, 90 from a source to the nozzles 62. In the example shown, a single coating flow 88 is provided through the feed plenum 84. In FIG. 1, two storage means 16, 18 are shown. There may be one or more separate coating materials provided, with only one coating being fed at a time by the pumping means 24 to the plenum 84. Alternatively, two constituent parts may be mixed to form the desired coating mixture directed through plenum 84. A valve 94 is connected to the plenum 84 at the position of the nozzle 62 to direct a portion of the coating flow 88 into the feed pipe 96, which is connected with the nozzle input 78. A valve controller 98 is provided to regulate flow from the plenum 84 to the nozzle input 78. The valve controller 98 is connected to the main controller (20, FIG. 1). A second valve 100 is provided on the carrier plenum 86. The second valve 100 directs a portion of the carrier flow 90 to the second inlet 80 on the body 76 of the nozzle 62. The second valve 100 includes a controller 102, which is also contemplated to be connected to the main controller (20).

FIGS. 2 and 7 generally show the position of multiple nozzles 62 relative to the trough 44 within the mixing chamber. As shown, eight (8) nozzles are provided, with all nozzles positioned above the first trough portion 44A. Any number of nozzles may be provided, depending on the size of the mixing chamber, the feed capabilities of the conveyor (30), the operational coating feed rates, the output capabilities of the nozzles, etc. The nozzle positioning is intended to create an incremental delivery of the coating material to the particulate material 34B within the first trough portion 44A of the mixing chamber. Additional mixing is performed by agitation of the particulate 34B within the second trough portion 44B. Each nozzle 62 is contemplated to be connected to the main coating flow 88 within the associated plenum 84 and the main carrier flow 90 within the second plenum 86. The input into the plenums 84, 86 from the pumps (24) may be located centrally within the line of nozzles (62) to assist in equalizing the flow to each nozzle. A valve (94, 100) and controller (98, 102) of the types shown in FIG. 6B are contemplated to be provided at each nozzle position, with each valve controller (98, 102) in communication with the main controller (20).

As illustrated, the contemplated spray pattern 64 is oval in shape and the adjacent nozzles are contemplated to create an overlapping pattern along the length of the trough portion 44A. Other spray patterns may be utilized as desired, in addition to variation in the number of spray nozzles. The plenum/manifold structures may be modified for directing flow to the nozzles. Multiple pump mechanisms may be provided in addition to metering means associated with the pumps. Additional plenums/manifolds may be provided for the further components of the coating mixture. For example, the properties of one or more a functional additives may necessitate their introduction into the mix at a position closely adjacent the nozzle. The materials may also require other special handling during delivery and mixing. It may also be advantageous in certain applications to provide other types of nozzles or other input structures to add materials, including coatings, carriers or otherwise, to the mixing particulate.

The discharge end 50 of the mixer 14 is shown in further detail in FIG. 8. The agitator shaft 46 extends through the discharge opening 56 and into a protective housing 74, which retains the bearing (52) and drive motor 26. (The paddle blades are not shown within this illustration for clarity of the other structures.) The discharge weir plate 60 is positioned between the opening 56 and the discharge end of the second trough portion 44B. The size and height of the weir 60 may be adjusted to control the flow of particulate material 34B from the mixing chamber. The weir 60 is generally intended to increase residence time of the mixing particulate 34B prior to discharge. The trough portion 44B is bolted or otherwise fixed to the end wall of the mixer housing 58. Preferably, the fixing means for the second trough portion 44B is externally accessible. The discharge conveyor 22 is positioned below the discharge opening 56 for directing the coated material (34C) away from the apparatus 10.

Figure 9:
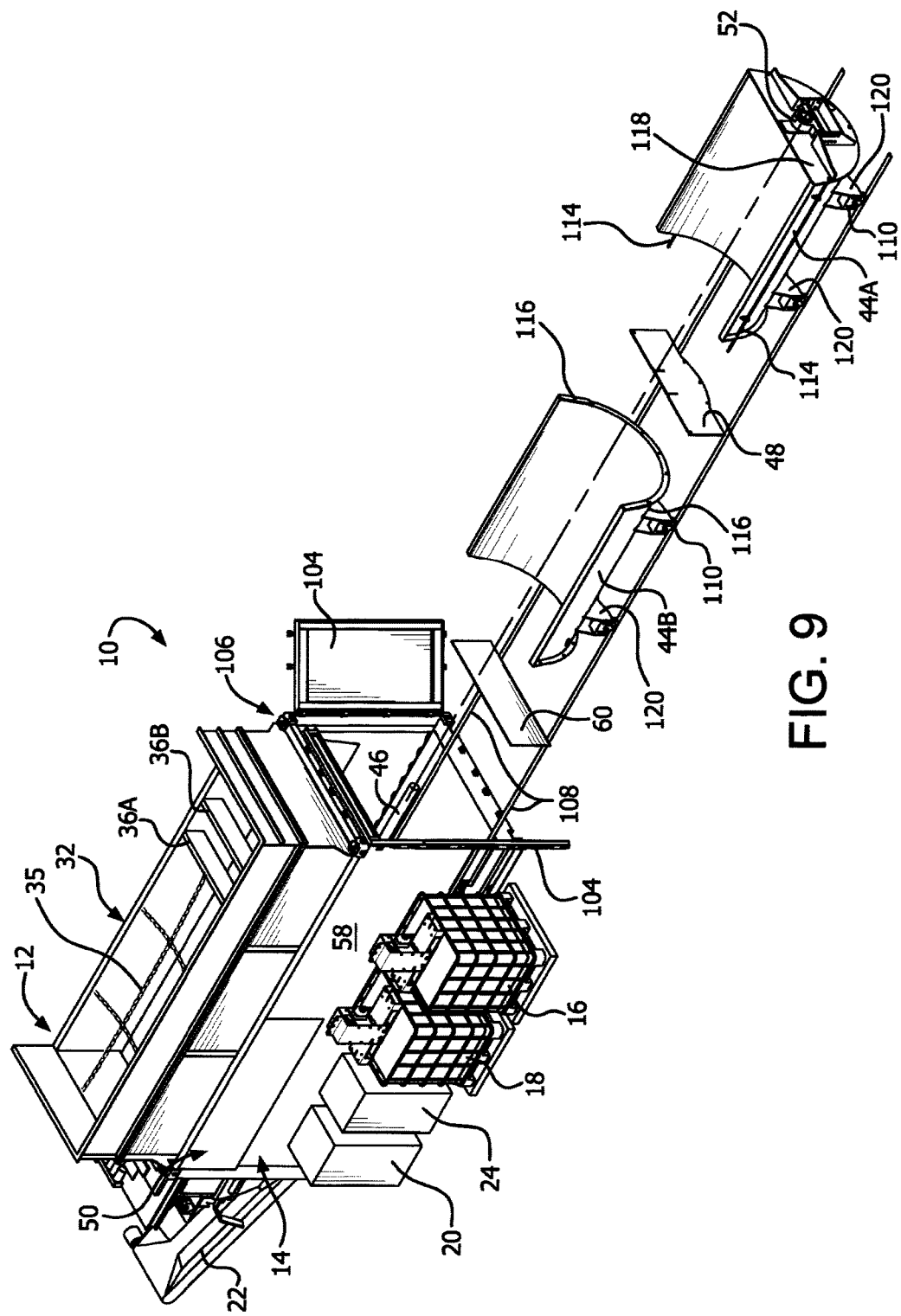
FIG. 9 shows an exploded, isometric view of constituent parts of the apparatus.

An exploded assembly of the mixer 14 is shown in FIG. 9. The trough 44 is separated into two sections 44A, 44B that are attached to one another and retained within the mixer housing 58. Doors 104 are provided at the inlet end 106 of the housing 58. Opening the doors 104 provides access to the assemblies within the mixing chamber, including the trough 44, the shaft 46 (and its associated paddles, not shown), the weir plates 48, 60, etc. The trough sections 44A, 44B are supported on rails 108 within the housing 58. The trough sections 44A, 44B include rollers 110 that ride on the rails 108 (see, also, FIGS. 1, 5 and 8.) Once the doors 104 are opened for access to the trough 44, the trough sections may be disconnected from one another, along with related structures, and removed from the housing 58. Rail extensions are shown for rolling of the first trough section 44A out of the housing after being detached from the second trough section 44B. The second section 44B may similarly be removed. As an alternative to the rail extensions (as shown), the trough sections may be removed from the housing 58 by a fork lift or other lifting mechanism as the trough is being rolled towards the open doors 104.

Rod members 114 are provided on the outside of the first trough section 44A. The rod ends engage a connector 116 on the second trough section 44B to retain the two sections together. The center weir plate 48 may be fixed to either trough section 44A, 44B and is engaged between the sections when secured by the rods 114 and connectors 116. Engagement and disengagement of the rods 114 from the connectors 116 is contemplated to be accomplished from a position adjacent the end wall 118 of the trough section 44A, without the need to move into the housing 58.

During removal of the trough 44, means for supporting the shaft 46 may be required. As shown, the end bearing 52 is supported on the end wall 118 of the first trough section 44A. In FIG. 9, the bearing 52 is separated from the shaft 46. As an alternative, the bearing 52 assembly may be removable from the end wall 118 and remain attached to the shaft 46. In either alternative, a support chain, or the like, may be fixed to the top of the housing 58 and used to suspend the shaft in position as the trough sections 44A, 44B are removed. The central bearing (54) is also contemplated to be detached from the weir plate 48 during disassembly. One or more inspection panels (not shown) may be provided within the housing 58 for access to the internal structures. Other access panels may be provided as desired. In addition, various covering structures may be provided for protection of various components during operation and for protection from the environmental conditions.

The clearance between the paddle blades 70 and the inside surface of the trough 44 is contemplated to be adjustable, for example, up to 10 centimeters (4 inches) or more. Such adjustments may serve to alter mix properties and to accommodate particulate material properties, such as particle size. The adjustment may also serve to reduce load on the drive motor (26) for the agitator. As shown in FIG. 8, the rollers 110 are formed as part of an assembly that is fixed to the trough 44B (and also 44A) by supports 120. The position of the roller 110 and assembly on the support 120 is adjustable. As shown, a series of holes 122 are provided on the support 120. Bolts 124 extend through the holes and engage the roller assembly. Adjusting the position of the bolts 124 within the holes 122 changes the relative position of the rollers 110. This change in position alters the height of the trough 44B (and 44A) relative to the height of the shaft 46 and alters the spacing between the paddle blades (70) and in inside surface of the trough 44. Adjustment of the attachment structures 126 fixing the trough 44B to the end wall of the housing 58 is also contemplated. Further, an accommodation must be made for the end bearing 52 on the end wall 118 of the first trough section 44A (see FIG. 9) due to the relative change in position of the shaft with respect to the trough 44. An adjustable mounting plate may be provided for fixing the bearing 52 to the end wall 118.

Generally, the various components of the apparatus (10) are controlled by the main controller (20). Coating materials are retained within the storage means (16, 18), which are connected to the internal flow plenum (84). The pump (24) is provided for metering the coating flow (88) from storage into the plenum (84). A separate carrier feed is provided and is connected with the pump (24) to provide a flow (90) to the second plenum (86). It is contemplated that a provided coating material, such as a colorant, a functional additive, a combination thereof or a combination of two or more functional additives, will include a set recipe for mixing with the water (or other carrier) to form a coating mixture (e.g., a colorant mixture or an additive mixture). This recipe will normally include a coating-to-carrier ratio (e.g., a colorant-to carrier ratio or an additive-to-carrier ratio) and a coating mixture flow (or coating, e.g., colorant or additive) flow) based on volume of particulate fed into the mixer. For example, in one embodiment the recipe may call for a certain amount (e.g., lbs) of coating per cubic yard (or kg per cubic meter) of particulate material to be processed. The controller (20) will be set with the parameters of the recipe by manual input or by selection from memory. Identification of the coating material(s) may be manually entered into the controller or may be identified by other means, such as the reading of an RFID chip or a bar code associated with the provided storage means (16, 18).

The typical coating is contemplated to be a mixture of, at least, one coating material and a water carrier. However, a single coating material may be applied without additional additives or a carrier. In such applications, the coating material (or single source mixture) will preferably be delivered to the nozzles (62) through the relatively high pressure, second plenum (86). The pressurized flow (90A) into the nozzle (62) will result in an atomized spray (64) at the outlet orifice (82).

In one particularly suitable embodiment, the controller is operable to control various operational parameters of the apparatus such that the end product (e.g., the coated particulate material) has a ratio of coating material to particulate material that is within ±5% of the predetermined recipe, or more broadly a predetermined target ratio as defined by the recipe. Various sensors may be provided through the apparatus to provide the controller with operational parameters and information sufficient to allow the controller to operate the apparatus in a manner that achieves the desired coating or recipe accuracy. The sensor signals will normally be processed by the controller and further control signals provided to adjust the operational elements of the apparatus. For example, in one suitable embodiment the volumetric flow rate of particulate material through the mixer, and more suitably in the illustrated embodiment the volumetric flow rate of particulate material into the mixing chamber, is intermittently determined and compared to a predetermined target volumetric flow rate of the particulate material through the mixer. If necessary, based on this comparison, the volumetric flow rate of particulate material fed into the mixing chamber is adjusted, e.g., by increasing or decreasing the speed at which particulate material is moved toward the inlet to the mixing chamber, to achieve a volumetric flow rate that is more indicative of the target volumetric flow rate of particulate material.

One or more of the operating parameters relating to delivery of the coating mixture (e.g., an additive mixture) into the mixing chamber are adjustable as a function of the adjustment to the volumetric flow rate of particulate material to the mixing chamber. For example, the flow rate of coating material to each nozzle, the flow rate of the carrier to each nozzle, the flow rate of the coating mixture (e.g., an additive mixture) from each nozzle, and the number of nozzles from which the coating mixture is emitted may be adjusted based on an adjustment of the volumetric flow rate of particulate material into (or, more broadly, through) the mixing chamber. This functional control based on adjustment of the volumetric flow rate of particulate material further facilitates achieving the desired recipe accuracy, e.g., within ±5% of the target coating (e.g., additive) to particulate ratio of the end product.

In operation, signals from the particulate feed means are utilized to control coating flow to the nozzles. The volume of particulate feed (34A) directed through the gate (38) and into the inlet (42) for the mixing chamber is measured. For example, in one embodiment the sensors 40 are used to read the depth, or height of the particulate material flowing beneath the sensors, such as at a rate of about once every 0.1 seconds. The controller 20 uses an accumulation of these measurements to intermittently determine the volumetric flow rate of particulate material into the mixing chamber (e.g., based also on the fixed width of the flow and the known speed at which the flow is moved toward the mixing chamber). In one embodiment, volumetric flow rate is determined by the controller 20 at a frequency of about once every 5 seconds. This relatively high frequency facilitates achieving the desired accuracy of the operating volumetric flow rate and hence the recipe accuracy of the end product. It is understood that in other embodiments another suitable frequency may be used for determining the volumetric flow rate.

Based on the volume of particulate matter added to the mixing chamber, the amount of coating material/mixture delivered from the nozzles is adjusted to match the recipe for the coating. Further, the carrier material is delivered to the nozzle at a constant (high) pressure for purposes of creating the desired atomized spray. The coating material is provided in an amount to match the carrier flow for the recipe.

In one preferred example of the operation of the apparatus 10, a rough-ground hardwood material, preferably mulch, is provided to form a feed particulate 34A. A functional additive, preferably selected from herbicides, insecticides, nutrients, wetting agents, surfactants, biologicals, inoculants and mixtures thereof is provided in either one or multiple storage means 16. For instance, if a colorant and a plant growth regulator are used in the process, separate storage means will be used in the process. The storage means could be used for preparing individual or multiple functional coatings. A further additive, such as a colorant, plant growth regulator, fragrance, etc. may be provided in the second storage means 18. The functional material recipe is input into the controller 20. The recipe will normally define the mix ratio for the functional material and the carrier, preferably water, the amount of coating mixture for a given volume of particulate feed, pump settings, conveyor settings, etc. After priming of the apparatus 10 and initiation of rotation of the agitator shaft 46, particulate feed 34A is deposited into the hopper 32 and the slat conveyor 30 is placed in operation. The feed material 34A moves under the gate 38, with the sensors 40 measuring height of the material flow. From the sensor data and conveyor speed data, a volumetric flow rate is determined for the particulate directed to the inlet 42 of the mixer 14. The particulate flow rate is then related to the coating mixture delivered by the nozzles 62.

In the embodiment shown, eight nozzles 62 are provided for directing the coating mixture onto the particulate 34B within the mixing trough 44. In operation, the carrier flow 90A directed to the nozzles 62 is delivered at a relatively high pressure. The pressure range is contemplated to fall between 551.6 to 1034.3 kPa (80 to 150 psi) for a high pressure operation. In one embodiment, a particularly suitable pressure is about 689.5 kPa (100 psi)±172.4 kPa (±25 psi). In another suitable embodiment a particularly suitable pressure is about 861.8 kPa (125 psi)±172.4 kPa (±25 psi). As such, the carrier flow serves as the atomizing agent for the coating mixture. The pressure of the carrier is contemplated to be maintained relatively constant. In determining the overall flow of coating mixture onto the mixing particulate 34B, adjustment of the quantity of coating mixture delivered to the mixing chamber is accomplished by controlling the number of nozzles in operation at any give time. The valves 94, 100 may be adjusted by the controller 20 to turn off a select number of nozzles 62. As an example, normal feed rates for the apparatus may result in the use of six nozzles 62, with two being turned off by the controller 20. An increase in demand for coating material will result in additional nozzles being turned on. A decrease in the particulate feed rate will result in additional nozzles being turned off Nozzle adjustment is based on the volume of particulate fed into the mixing chamber and the coating recipe. The recipe will at a minimum be set to the kilograms per minute (kg/min) of coating and a corresponding liters per minute (l/min) of the carrier for a particulate feed rate in cubic meters per minute (m3/min). Measuring the pressure of the carrier flow is correlated to the l/min of carrier delivered to the nozzles. In keeping the pressure of the carrier constant (i.e., within a preset range), the carrier flow through each nozzle is relatively constant. On an increasing demand for coating mixture (due to an increase in volumetric particulate feed rate), additional carrier and coating is required. The controller determines the additional coating needs feed and initiates operation of one or more additional nozzles. The addition of operational nozzles is combined with an adjustment of the pumps 24, feeding the coating material from the storage means 16 (and/or 18) and the carrier (water) from its associated supply. The carrier pump is also adjusted through the controller 20 to maintain the pressure of the flow 90 within the preset range delivered to the nozzles 62 in operation.

The spray pattern 64 from the nozzles 62 preferably directs the coating mixture onto the particulate 34B along the first half of the longitudinal length of the trough 44. The speed of the agitator shaft 46, the position and number of paddle blades 70, the size and position of the weir plates 48, 60 all serve to affect the overall mixing and conveying operation and the further overall residence time of the mixing particulate within the trough 44. It is contemplated that the nozzles 62 being adjusted on and off will be typically located adjacent the central weir plate 48. Hence, the application of coating mixture by the nozzles will occur at the initial part of the mixing chamber with agitation continuing to occur in the downstream end of the trough 44. Other nozzle positions and alignments may be utilized to regulate flow, as well as to maintain a relatively consistent mixture between the coating materials and (any) carrier delivered by the various nozzles.

The controller 20 maintains the flow of coating by adjustment of the provided pump(s) 24 connected to the storage means 16, 18. For example, the storage means 16, 18 in which the coating (e.g., colorant or additive) is stored may be provided with a scale to determine (e.g., as the volumetric particulate flow rate is determined) the weight of the coating material and hence an actual volumetric flow rate of the coating material from the storage means to the nozzles. The actual volumetric flow rate of the coating material is compared to a theoretical volumetric flow rate (e.g., based on the volumetric flow rate of the particulate material into the mixing chamber). The weight change of the stored coating material may thus be used to create a correction to the pump operation, based on the desired recipe. Other forms of measurement for the concentrate may also be used. Adjustments based on manual or sensor input, may be made during operation through the controller 20. Further, adjustments to the particulate feed provided by the conveyor 30 may be accomplished during processing to affect the overall coating operation. Generally, a change in the particulate feed rate delivered to the mixing chamber will vary the load on the agitator and may used to bring the coating mixture feed in line with a desired performance range.

The use of a pressurized carrier flow as an atomizer for a coating mixture is contemplated to create a number of advantages. First, a separate gas compressor for gas (air) atomization of the spray is not required. The elimination of the gas compressor reduces the overall power requirements for the apparatus. In addition, it has been found that the controlled nozzle feed and carrier atomized spray may reduce the overall requirements for carrier, preferably water, and the coating material. This reduction in coating use may result in part from the relatively larger atomized particles formed by the carrier atomized coating mixture, as compared to the coating particles formed through a gas atomization process. The relatively larger particles improve distribution of the coating through a higher impact (a function of the mass of the particle and the speed at impact). Ultimately, the use of less of the water or other carrier, within a relatively faster mixing operation, reduces processing time for the coated particulate after discharge from the apparatus. For example, because of the overall use of less water, the coated particulate may be moved more quickly to a bagging operation. An extended mixing (retention time) within the overall operation may further result in better adhesion of the coating and relatively uniform coating of the particulate. Other advantages are contemplated and may be apparent to those of skill in the relevant art after reviewing the present disclosure.

The process for coating particulate material according to the present invention is particularly suited for the preparation of functionalized coatings on mulch material, preferably obtained from wood. In other words, mulch is a preferred particulate material.

The term "mulch" as used in the present invention relates to any material applied to the surface of an area of soil for any number of purposes, including plant growth enhancement, moisture conservation, improvement of soil health and fertility, weed growth reduction, or visual appeal enhancement. Mulch can include any type of ground cover, including wood, paper, grass, hay, straw, pellets, organic residues, rubber, plastic, or rock and gravel.

In certain embodiments, the mulch can be wood mulch from wood of any type, including hard wood, softwood, or recycled wood. The wood mulch can be ground wood mulch of any grind size or mix of grind sizes or chipped wood mulch of any chip size or mix of chip sizes. The pellet mulch can be made up of natural fiber pellets or any other known pellet for a mulch product.

According to certain implementations, the organic residue mulch can be made of grass clippings, leaves, hay, straw, shredded bark, whole bark nuggets, sawdust, shells, woodchips, shredded newspaper, cardboard, or any other known organic residue used in mulch products. In one embodiment, the rubber mulch can be made from recycled tire rubber or any other known type or source of rubber that is used in mulch products. Further, the plastic sheet mulch can be any known mulch product in the form of a plastic sheet, including, for example, the type of plastic sheet mulch used in large-scale vegetable farming. In certain embodiments, mulch is any functional ground cover.

Another alternative particulate material that is coated by use of the process according to the present invention for providing a functionalized coating is potting soil.

It is understood that "potting soil" also known as potting mix, or potting compost, means any material or medium in which to grow plants. Some common ingredients used in potting soil are peat, composted bark, soil, sand, sandy loam (combination of sand, soil and clay), perlite or vermiculate and recycled mushroom compost or other aged compost products although many others are used and the proportions vary hugely. Most commercially available potting soils have their pH fine-tuned with ground limestone, some contain small amounts of fertilizer and slow-release nutrients. Potting soil recipes are known e.g. from US 2004/0089042 A1. Commercially available potting soil is sterilized, in order to avoid the spread of weeds and plant-borne diseases. Packaged potting soil often is sold in bags ranging from 1 to 50 kg.

The coated particulate material comprising the functional coating as obtained by the process according to the present invention can be applied as a layer to the soil around or in the vicinity of any number of different types of plants. For example, in one implementation, the composition can be applied to common landscape plants, including, but not limited to, trees, shrubs, woody ornamentals, herbaceous perennials, ornamental grasses and ground covers, ornamental bedding plants, vegetables, as well as plants grown for their fruits like blueberry, strawberry and raspberry. Further, it is understood that the coated particulate material obtained by the process according to the present invention can be applied to any known plant that benefits from application of mulch. Alternatively, the composition can be applied as a layer to bare soil (where no plants are present). Alternatively, the mulch composition can be applied as a layer to soil in the vicinity of a location where a plant is to be grown (e.g. plant propagation material is sown). In one embodiment, the mulch composition is applied to the soil as a layer having a thickness ranging from about 0.5 to about 15 cm. Alternatively, the layer has a thickness ranging from about 2.5 to about 10 cm. In a further alternative, the layer has a thickness of at least 5 cm.

According to one embodiment, the coated particulate material obtained by the process according to the present invention can be applied to soil and/or into a container, followed by planting one or more growing plants within the potting soil composition or sowing one or more plant propagation materials within the potting soil composition.

The terms "plant", or "plants" as used herein are to be understood as including but not be limited to cultivated plants, such as cereals, e. g. wheat, rye, barley, triticale, oats or rice; beet, e. g. sugar beet or fodder beet; fruits, such as pomes, stone fruits or soft fruits, e. g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called *Stevia*); natural rubber plants or horticultural or ornamental and forestry plants, such as flowers, shrubs, broadleaved trees or evergreens, e. g. conifers; including the plant propagation material, such as seeds.

The term "plant propagation material" is to be understood to denote all the generative parts of the plant such as seeds and vegetative plant material such as cuttings and tubers (e. g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil.

The term "cultivated plants" is to be understood as including plants which have been modified by breeding, mutagenesis or genetic engineering including but not limiting to agricultural biotech products on the market or in development (cf. http://cera-gmc.org/, see GM crop database therein). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e. g. by glycosylation or polymer additions such as prenylated, acetylated or farnesylated moieties or PEG moieties.

The present disclosure includes a description and illustration of a number of exemplary embodiments. The following embodiments are preferred embodiments for the apparatus according to the present invention used for carrying out the process of providing a functional coating to a particulate material, preferably a landscape material like for instance mulch and similar wood materials.

A preferred apparatus to be used in the inventive process for coating a particulate material, preferably with a functional coating, comprises:

a mixer having a mixing chamber;

means for feeding the particulate material into the mixing chamber;

an agitator provided in the mixing chamber, the agitator mixing and conveying the particulate material from an inlet to a discharge outlet;

a coating feed system for delivery of a coating into the mixing chamber during mixing by the agitator, the coating delivered as an atomized spray directed at the mixing particulate material within the mixing chamber; and a controller for adjusting the flow of the coating into the mixing chamber based on the volumetric flow rate of the particulate material.

In a further preferred embodiment of the apparatus, the feeding means is a slat conveyor.

In a further preferred embodiment of the apparatus, the agitator is formed by a rotating shaft having a plurality of paddle blades positioned on arms projecting from the shaft.

In a further preferred embodiment of the apparatus, the coating comprises a mixture of a coating material and a pressurized carrier.

In a further preferred embodiment of the apparatus, the pressurized carrier is water.

In a further preferred embodiment of the apparatus, the pressurized carrier is provided at about 689 kPa.

In a further preferred embodiment of the apparatus, the apparatus further comprises sensors providing signals proportional to the volume of particulate material fed from the feeding means to the mixing chamber.

In a further preferred embodiment of the apparatus, the sensor signals are combined with signals from the feeding means to determine the volumetric flow rate of the particulate material.

In a further preferred embodiment of the apparatus, the controller receives sensor signals and the feeding means signals and directs a control signal to the coating feed system to adjust the flow of the coating into the mixing chamber.

In a further preferred embodiment of the apparatus, the coating feed system comprises a plurality of spray nozzles.

In a further preferred embodiment of the apparatus, the spray nozzles direct the spray within an initial portion of the length of the mixing chamber.

In a further preferred embodiment of the apparatus, adjustment of the flow rate of the spray from the plurality of nozzles by the controller is performed by regulating the number of operational spray nozzles.

In a further preferred embodiment of the apparatus, each of the spray nozzles comprises a separate inlet for a coating material and for a carrier material and wherein a coating mixture of the coating material and carrier is formed by the spray nozzle at an outlet orifice.

In a further preferred embodiment of the apparatus, the carrier material of the coating mixture is pressurized at the carrier material inlet to the spray nozzle and wherein the pressurized carrier creates the atomized spray at the outlet orifice.

In a further preferred embodiment of the apparatus, the adjustment of the flow rate of the coating spray is based on a preset ratio of kilograms per minute (kg/min) of a coating material and liters per minute (l/min) of a carrier material to the feed rate in cubic meters per minute (m3/min) of the particulate material.

In a further preferred embodiment of the apparatus, the mixing chamber is defined in part by an elongated trough.

In a further preferred embodiment of the apparatus, at least one weir plate is provided within the trough for increasing residence time of the particulate within the mixing chamber.

It should be understood by those skilled in the art from the foregoing that various other changes, omissions and additions may be made therein, without departing from the spirit and scope of the invention, with the invention being identified by the foregoing.

A preferred embodiment of the apparatus for performing the process according to the present invention for preparing functionally treated particulate material having a coating of functional material has been described above.

The present invention is further illustrated by the following examples which are however not intended to limit the scope of the present invention.

In all screening tests, the functional treatment of particulate material was conducted using a Sahara PRO apparatus comprising a mixer having a mixing chamber;
means for feeding the particulate material into the mixing chamber; The feed means for the particulate material comprises a hopper having a floor forming a conveyor for moving the particulate material to the mixing chamber via the mixing chamber inlet.

an agitator provided in the mixing chamber, the agitator mixing and conveying the particulate material from an inlet to a discharge outlet;

a coating feed system for delivery of a coating into the mixing chamber during mixing by the agitator, the coating delivered as an atomized spray directed at the mixing particulate material within the mixing chamber; and The coating feed system comprises a pump., any desired form of pump may be used, e.g. peristaltic.

a controller for adjusting the flow of the coating into the mixing chamber based on the volumetric flow rate of the particulate material. Controlling the volumetric flow rate of the coating spray is based on a present ratio of kilograms per minute (kg/min) of a coating material and liters per minute (l/min) of a carrier material to the flow rate in cubic meters per minute ($m^3$/min) of the particulate material.

During this functional treatment, the particulate material as used in all screening tests was coated using a Sahara PRO apparatus comprising the steps of:

feeding the particulate material into the mixing chamber;

agitating the particulate material within the mixing chamber and conveying the mixing particulate material to a mixing chamber outlet;

directing an atomized coating spray into the mixing chamber, the spray directed at the agitating and conveying particulate material at a plurality of defined locations within the mixing chamber; and atomization is achieved by pressurizing the carrier component, preferably water and delivering the pressurized carrier component to the coating component to create the atomized coating spray at a pressure in the range of 552 kPa to 1034 kPa.

controlling the flow rate of coating spray based on the volumetric flow rate of the particulate material into the mixing chamber characterized in that the coating spray comprises at least one compound selected from herbicides, insecticides, nutrients, wetting agents, surfactants, fungicides, biologicals, inoculants, and mixtures thereof.

EXAMPLES

Screening test 1: Evaluation of colored and non-colored mulch functionalized with additional herbicide for weed control.

The following functionalized treatments were prepared—Hardwood, 2" (5.08 cm) mulch depth (1× rate):

Non-colored (raw) mulch; lacking any functional treatment with herbicide (comparative example CE1);

Raw mulch functionalized with herbicide using the process according to the present invention (combination of herbicides pendimethalin and dimethenamid-P) (inventive example IE1);

Colored mulch; no functional treatment with herbicide (comparative example CE2);

Colored mulch functionalized with herbicide (combination of herbicides pendimethalin and dimethenamid-P) using the process according to the present invention (inventive example IE2);

Preen Mulch Plus; a comparative mulch product containing granules in mulch bag (not attached to mulch) (comparative example CE3);

FreeHand®—a commercial material containing the herbicides pendimethalin and dimethenamid-P in granular form (comparative example CE4);

Pine straw; lacking any functional treatment (comparative example CE5);

Using the process for providing a functionalized coating to a particulate material according to the present invention, a combination of the herbicide liquids was applied to mulch with and without colorant (named inventive examples IE1 and IE2). The amounts were as follows:

| Herbicide actives | a.i. in herbicide formula | Rate of liquid herbicide/ft$^3$ of mulch | a.i. of mulch |
| --- | --- | --- | --- |
| Pendimethalin | 455 g/L | 0.7 grams | 0.0036 wt % |
| Dimethenamid-P | 720 g/L | 0.15 grams | 0.0013 wt % |

Evaluation of the functionalized particulate materials according to the present invention (inventive examples IE1 and IE2) was carried out relative to the comparative examples CE1 to CE5 based on a screen for weed efficacy of the corresponding materials.

In the initial screening experiment, the effect of the functional treatment of the particulate materials according to inventive examples IE1 and IE2 relative to the comparative materials according to comparative examples CE1 to CE5 were tested for the following three different weeds:

Velvetleaf—small seeded broad leaf weed (ABUTH, *Abutilon theophrasti*)

Ryegrass—grass (LOLPE, *Lolium perenne*)

Crabgrass—grass (DIGSA, *Digitaria sanguinalis*)

The results of this screening experiment are depicted in the below Table 1.

Table 1 shows the results of a screening experiment related to weed control using a functional herbicide coating on particulate material.

TABLE 1

(all numeric values are % weed control):

| | ABUTH | LOLPE | DIGSA |
| --- | --- | --- | --- |
| Pine Straw (comparative example CE5) | 36 | 45 | 55 |
| Preen Mulch Plus (comparative example CE3) | 71 | 93 | 94 |
| Colored mulch treated (inventive example IE2) | 100 | 100 | 100 |
| Colored mulch (comparative example CE2) | 64 | 40 | 88 |
| Raw mulch treated (inventive example IE1) | 100 | 100 | 100 |
| Raw mulch (comparative example CE1) | 52 | 35 | 90 |
| FreeHand G (comparative example CE4) | 66 | 93 | 100 |
| Check (i.e. no mulch, no treatment) | 0 | 0 | 0 |

(Legend to Table 1: ABUTH = Velvetleaf – small seeded broad leaf weed; LOLPE = Ryegrass – grass; DIGSA = Crabgrass – grass)

The following conclusions can be drawn from this screening experiment:

Both colored and raw treated mulches that have been provided with a functionalized coating using the process according to the present invention provide the best weed control.

An additional color treatment does not appear to affect the efficacy of the functionalized coating according to the present invention.

For all the screening tests with herbicide compositions or mixtures, the examplary, non-limiting application recipe is as follows:

| | |
| --- | --- |
| Carrying Agent (water) | 370 lbs [168 kg] |
| Herbicide A (active ingredient pendimethalin at 455 g/L) (5 gal [18.9 L]) | 51.3 lbs [23.3 kg] |
| Herbicide B (active ingredient dimethenamid-P at 720 g/L) (1.1 gal [4.2 L]) | 11.0 lbs [4.9 kg] |
| Total net weight after mix | 432 lbs [196 kg] |
| Gross weight with drum (24 lbs [11 kg]) | 456 lbs [207 kg] |

For all the screening tests with herbicide compositions or mixtures, the application rates for Sahara are as follows:

| | |
| --- | --- |
| Colorant (Mulch Magic Series) | 3.2-4.2 lbs/yd$^3$ [1.9 – 2.5 kg/M$^3$] |
| Herbicide Additive | 0.35 lbs/yd$^3$ [207.7 g/M$^3$] |
| Water | 10-25 gal/yd$^3$ [50 – 124 L/M$^3$] |

One drum of herbicide additive should produce 1,233 cubic yards (943 cubic meters) of wood mulch.

Mixing machines volumetrically monitor wood mulch input to calculate application rates.

Screening test 2: Evaluation of weed control using functionalized particulate material in view of various types of weed.

The percentages of the weed control were determined via visual assessment.

The following samples were prepared—Hardwood, 2" (5.08 cm) mulch depth (1× rate):

Treatments: Combined active rate: 0.004 wt %; Hardwood mulch 2" (5.08 cm) depth.

Raw mulch, lacking functionalization with herbicide (Comparative example CE 6);

Colored mulch functionalized with herbicide (combination of herbicides pendimethalin and dimethenamid-P) using the coating process according to the present invention (Inventive example IE 3);

Preen Mulch Plus, a comparative mulch product containing granules in mulch bag (Comparative example CE 7)

Weed* Control > 90 Days After Treatment – varied locations

| Treatment | Crabgrass | Crabgrass | Spurge | Bittercress | Chickweed |
| --- | --- | --- | --- | --- | --- |
| Comparative example CE 6 | 63 | 67 | 93 | 100 | 100 |
| Inventive example IE 3 | 99 | 100 | 100 | 100 | 100 |
| Comparative example CE 7 | 97 | 87 | 100 | 100 | 100 |
| Location | 1 | 2 | 1 | 1 | 1 |

Acceptable > 85%, Marginal 70 – 84%, Unacceptable < 69% control
*Crabgrass = *Digitaria* spp.; Spurge = *Euphorbia* sp.; Bittercress = *Cardamine* sp.; Chickweed = *Stellaria media*

Weed* Control > 90 Days After Treatment – varied locations

| Treatment | Pigweed | Lambsquarters | General weed | Asiatic elm |
| --- | --- | --- | --- | --- |
| Comparative example CE 6 | 78 | 98 | 20 | 27 |
| Inventive example IE 3 | 100 | 100 | 100 | 98 |
| Comparative example CE 7 | 66 | 100 | 100 | 100 |
| Location | 2 | 3 | 4 | 3 |

Acceptable > 85%, Marginal 70 – 84%, Unacceptable < 69% control
*Pigweed = *Amaranthus* sp.; Lambsquarters = *Chenopodium album*; Asiatic elm = *Ulmus pumila*.

| Weed* Control 30-45 Days After Treatment – varied locations | | | | | | |
|---|---|---|---|---|---|---|
| Treatment | Night-shade | Pig-weed | Goose-grass | Yellow nutsedge | Fox-tail | Y Nut-sedge |
| Comparative example CE 6 | 53 | 91 | 50 | 0 | 73 | 43 |
| Inventive example IE 3 | 86 | 100 | 100 | 85 | 99 | 99 |
| Comparative example CE 7 | 49 | 90 | 100 | 0 | 99 | 98 |

Acceptable > 85%, Marginal 70 – 84%, Unacceptable < 69% control
*Nightshade = *Solanum* sp.; Pigweed = *Amaranthus* sp.; Goosegrass = *Eleusine indica*; Yellow nutsedge = *Cyperus esculentus*; Foxtail = *Setaria* sp.

The following conclusions could be drawn from this screening experiment:
  The effect of weed control is successfully achieved when the combination of herbicide and colorant is applied to the particulate material.
  The effect is achieved for a broad spectrum of weeds, the residual is appropriate for at least one season.

Screening test 3: Evaluation of tolerance of plants against functionally treated particulate material.

This test was carried out using a larger number of different ornamentals. Tolerance was studied at 1.5× rate=3 inches of functionally treated particulate material (mulch). The following ornamentals were included in this test experiment:
 a) Annuals: *Zinnia, Petunia, Impatiens*, Snapdragon, Ice Plant, Summer Snapdragon;
 b) Perennials: Black-eyed Susan, Shasta Daisy, Hosta, Daylily, Coral Bells, Azalea, Periwinkle;

Results:
No injury could be identified for the above ornamentals at any location;
No injury could be identified for any species.

Screening test 4: Recovery of functional material from particulate material. In this experimental study the herbicide active ingredient was analyzed as the content of functional material (herbicide) as the active ingredient in the particulate material (mulch).

Assay protocol: Ten milliliters of 100% methanol was used to extract the herbicide actives, Pendimethalin and Dimethenamid-P from one gram of mulch. Methanol and mulch were added to a vial and shaken at approximately 180 rpm for 30 minutes on a shaker table. Methanol was filtered from mulch and analyzed for actives via HPLC. Active ingredient recovery was recorded as weight percent. Mulch samples were taken from top and bottom of weathered mulch beds at 3.5 months.

The results of this screening experiment are depicted in below Table 2 and Table 3. Table 2 and Table 3 show the results of an experiment related to the recovery of herbicide active ingredient from particulate material after providing functional herbicide coating. Table 2 and Table 3 show active ingredient releasing from the mulch at one month exposure compaed to non-exposed mulch in warehouse.

TABLE 2

| (all numeric values are weight percent of pendimethalin): | | | |
|---|---|---|---|
| | Red mulch | Black mulch | Natural mulch |
| Bottom 1 month | 0.00026 | 0.00005 | 0.00026 |
| Standard deviation for Bottom 1 month | 0.00003 | 0.00003 | 0.00012 |
| Top 1 month | 0.00054 | 0.00044 | 0.00079 |
| Standard deviation for Top 1 month | 0.00002 | 0.00014 | 0.00036 |
| Warehouse | 0.00302 | 0.00440 | 0.00674 |
| Standard deviation for warehouse | 0.00070 | 0.00062 | 0.00212 |

TABLE 3

| (all numeric values are weight percent of dimethenamid-P): | | | |
|---|---|---|---|
| | Red mulch | Black mulch | Natural mulch |
| Bottom 1 month | 0.00000 | <LOD | <LOD |
| Standard deviation for Bottom 1 month | 0.00000 | 0.00000 | 0.00000 |
| Top 1 month | 0.00002 | 0.00003 | 0.00004 |
| Standard deviation for Top 1 month | 0.00001 | 0.00001 | 0.00000 |
| Warehouse | 0.00233 | 0.00200 | 0.00203 |
| Standard deviation for warehouse | 0.00037 | 0.00003 | 0.00052 |

The following conclusions could be drawn from this screening experiment based on the results summarized in Table 2 and Table 3:
  The herbicides used in this screening test released from the mulch.

Screening test 5: Evaluation of efficacy of colored and non-colored mulch (wood fiber) functionalized with insecticide:
Alpine WSG containing as the active ingredient the insecticide dinotefuran and Fastac CS containing as the active ingredient alpha-cypermethrin were used in these tests.

An exemplary, non-limiting procedure of insecticide treatment of mulch is provided below:

| | |
|---|---|
| Impact Coffee Brown (colorant) | 375 lbs [170 kg] |
| Alpine WSG (ai dinotefuran 40% (w/w)) | 1.07 lbs [0.77 kg] |

Mixing vessel was a 35 gallon drum containing 375 pounds of Impact Coffee Brown colorant. The colorant was mixed for 20 minutes with a drum mixer to insure uniformity of colorant. After mixing color, 1.07 pounds of Alpine WSG was added. This mixture was stirred for 20 minutes using a drum mixer. The drum containing colorant and insecticide was immediately hooked-up to Sahara PRO for application to particulate material.

| | |
|---|---|
| Color rate | 3.50 lbs/yd$^3$ [2.076 kg/m$^3$] |
| Insecticide rate | 0.01 lbs/yd$^3$ [0.006 kg/m$^3$] |
| Mixture was applied at | 3.51 lbs/yd$^3$ [2.082 kg/m$^3$] |

| hardwood substrate | active ingredients | insects |
|---|---|---|
| non-colored (raw) mulch without insecticide, raw mulch with insecticide, colored mulch with insecticide | dinotefuran, alpha-cypermethrin | red imported fire ants (RIFA), argentine ants (Arg. Ants), odorous house ants (O.H. ants) | insecticides applied to mulch with and without colorant

| insecticide actives | a.i. in formula | rate of insecticide/ft³ mulch | a.i. on mulch (1x = label rate) |
|---|---|---|---|
| dinotefuran | 40 wt % | 0.18 grams | 0.0011 wt % |
| alpha-cypermethrin | 100 g/L | 0.05 grams | 0.0008 wt % |

Methods:

Testing with red imported fire ant (*Solenopsis invicta*, RIFA), Argentine ant (*Linepthema humile*), and odorous house ant (OHA) workers. Ten inch plastic arenas (inside walls coated with Fluon® to prevent escape) were provided a layer of moistened play sand. A band of mulch was placed across the arena near one side. Between the closest side and the mulch, a micro-centrifuge tube with a universal ant diet was placed. In the larger open area of the arena was placed a water vial and a small weigh boat with either corn grit+soybean oil (RIFA) or 20% honey water (Argentine ant and OHA). Approximately 100 ants were placed in each arena. Mortality was evaluated at 6 or 7 days.

Results from efficacy screen

| | | | | Mean % Mortality | | |
|---|---|---|---|---|---|---|
| Treatment | X label rate | Grams/ ft³ | a.i. wt % on mulch | RIFA 6 Days | Arg. Ants 7 Days | O.H. Ants 7 Days |
| Alpine WSG | 2 | 0.36 | 0.0022 | 98.3 | 93.9 | 0.0 |
| | 5 | 0.9 | 0.0056 | 100.0 | 100.0 | 19.0 |
| Fastac CS | 2 | 0.1 | 0.0016 | 39.7 | 1.6 | 0.0 |
| | 5 | 0.25 | 0.0039 | 87.7 | 5.9 | 0.0 |
| Non-treated | — | — | — | 1.1 | 2.3 | 0.0 |

Conclusions:
Both insecticides tested were highly effective when used on functionalized mulch.
Alpine WSG (dinotefuran) was the most effective insecticide.

Insecticide rate evaluation (against red imported fire ant (*Solenopsis invicta*) workers)

| | X label | | a.i. wt % | Mean % Mortality | |
|---|---|---|---|---|---|
| Treatment | rate | grams/ft³ | on mulch | 7 Days | 13-14 Days |
| Alpine WSG | 0.5 | 0.09 | 0.0006 | 51.6 | 56.0 |
| (dinotefuran) | 1 | 0.18 | 0.0011 | 69.5 | 99.0 |
| | 1.5 | 0.27 | 0.0017 | 68.0 | 100.0 |
| | 2 | 0.36 | 0.0022 | 54.3 | 92.9 |
| | 2.5 | 0.45 | 0.0028 | 59.3 | 93.0 |
| | 3 | 0.54 | 0.0038 | 73.2 | 97.4 |
| Non-treated | — | — | — | 2.6 | 5.5 |

Conclusions:
Red or black colored mulch does not appear to affect efficacy of the insecticide when compared to raw mulch.
The active ingredient dinotefuran was effective at all rates tested.
The most effective rate for dinotefuran appears to be between 1 and 1.5 label rates and 0.001 to 0.006 wt % based on the particulate material.

The present disclosure includes a description and illustration of a number of exemplary embodiments. It should be understood by those skilled in the art from the foregoing that various other changes, omissions and additions may be made therein, without departing from the spirit and scope of the invention, with the invention being identified by the foregoing claims.

What is claimed is:

1. A method of applying a functional additive to a particulate landscaping material, the method comprising:
feeding a particulate landscaping material into a mixing chamber from a hopper, the hopper comprising two opposing sides, a baffle, a conveyor, and a sensor, the two opposing sides, the baffle, and the conveyor defining a gate;
delivering a flow of additive mixture to a plurality of spray nozzles within the mixing chamber, the additive mixture comprising a functional additive and a carrier;
operating at least one of the plurality of spray nozzles to direct an atomized spray of additive mixture into the mixing chamber for contact with particulate landscaping material in the mixing chamber;
agitating the particulate landscaping material within the mixing chamber at least one of during and after directing the atomized spray of additive mixture into the mixing chamber;
conveying the particulate landscaping material with the additive mixture applied thereto to a mixing chamber outlet;
during the feeding, delivering, operating, agitating and conveying steps, intermittently determining a volumetric flow rate of the particulate landscape material through the mixing chamber by measuring the volumetric flow rate of the particulate landscape material through the gate with the sensor;
intermittently comparing the determined volumetric flow rate of the particulate landscape material to a predetermined target flow rate of the particulate landscape material;
adjusting, based on said comparing, the volumetric flow rate of the particulate landscape material through the mixing chamber by adjusting the volumetric flow rate of the particulate landscape material through the gate.

2. The method set forth in claim 1 further comprising the step of adjusting, based on each adjustment of the volumetric flow rate of the particulate landscape material through the mixing chamber, at least one of a flow rate of the additive mixture to the plurality of spray nozzles, a flow rate of the carrier to the plurality of spray nozzles, a flow rate of the additive mixture to the plurality of spray nozzles and the number of spray nozzles that are operated to direct an atomized spray into the mixing chamber.

3. The method set forth in claim 1 wherein the steps of intermittently comparing the determined volumetric flow rate of the particulate landscape material to a predetermined target flow rate of the particulate landscape material and adjusting, based on said comparing, the volumetric flow rate of the particulate landscape material through the mixing chamber, are performed at a frequency of at least once every 5 seconds.

4. The method set forth in claim 3 wherein the step of intermittently determining a volumetric flow rate of the particulate landscape material through the mixing chamber during the feeding, delivering, operating, agitating and conveying steps is performed at a frequency greater than the frequency at which the steps of intermittently comparing the determined volumetric flow rate of the particulate landscape material to a predetermined target flow rate of the particulate landscape material and adjusting, based on said comparing, the volumetric flow rate of the particulate landscape material through the mixing chamber are performed.

5. The method set forth in claim 4 wherein the step of intermittently determining a volumetric flow rate of the particulate landscape material through the mixing chamber during the feeding, delivering, operating, agitating and conveying steps is performed at a frequency of approximately once every 0.1 seconds.

6. The method set forth in claim 1 wherein the steps of intermittently comparing the determined volumetric flow rate of the particulate landscape material to a predetermined target flow rate of the particulate landscape material and adjusting, based on said comparing, the volumetric flow rate of the particulate landscape material through the mixing chamber, is performed at a frequency sufficient to achieve a ratio of additive to particulate landscape material that is within 5% of a predetermined target ratio of additive to particulate landscape material.

7. The method set forth in claim 1 wherein the step of intermittently determining a volumetric flow rate of the particulate landscape material through the mixing chamber during the feeding, delivering, operating, agitating and conveying steps comprises determining a volumetric flow rate of the particulate landscape material during the feeding step as the particulate landscape material is delivered into the mixing chamber.

8. The method set forth in claim 1, wherein the functional additive comprises an herbicide.

9. The method set forth in claim 8 wherein the herbicide is selected from:
acetamides selected from the group consisting of acetochlor, alachlor, butachlor, dimethachlor, dimethenamid, flufenacet, mefenacet, metolachlor, metazachlor, napropamide, naproanilide, pethoxamid, pretilachlor, propachlor, thenylchlor;
amino acid derivatives selected from the group consisting of bilanafos, glyphosate, glufosinate, sulfosate;
aryloxyphenoxypropionates selected from the group consisting of clodinafop, cyhalofop-butyl, fenoxaprop, fluazifop, haloxyfop, metamifop, propaquizafop, quizalofop, quizalofop-P-tefuryl, bipyridyls selected from the group consisting of diquat, paraquat;
(thio)carbamates selected from the group consisting of asulam, butylate, carbetamide, desmedipham, dimepiperate, eptam (EPTC), esprocarb, molinate, orbencarb, phenmedipham, prosulfocarb, pyributicarb, thiobencarb, triallate;
cyclohexanediones selected from the group consisting of butroxydim, clethodim, cycloxydim, profoxydim, sethoxydim, tepraloxydim, tralkoxydim;
dinitroanilines selected from the group consisting of benfluralin, ethalfluralin, oryzalin, pendimethalin, prodiamine, trifluralin;
diphenyl ethers selected from the group consisting of acifluorfen, aclonifen, bifenox, diclofop, ethoxyfen, fomesafen, lactofen, oxyfluorfen;
hydroxybenzonitriles selected from the group consisting of bomoxynil, dichlobenil, ioxynil;
imidazolinones selected from the group consisting of imazamethabenz, imazamox, imazapic, imazapyr, imazaquin, imazethapyr;
phenoxy acetic acids selected from the group consisting of clomeprop, 2,4-dichlorophenoxyacetic acid (2,4-D), 2,4-DB, dichlorprop, 2-methyl-4-chlorophenoxyacetic acid, 2-methyl-4-chlorophenoxyacetic acid- thioethyl, 4-(4-chloro-o-tolyloxy)butyric acid, Mecoprop;

pyrazines selected from the group consisting of chloridazon, flufenpyr-ethyl, fluthiacet, norflurazon, pyridate;
pyridines selected from the group consisting of aminopyralid, clopyralid, diflufenican, dithiopyr, fluridone, fluroxypyr, picloram, picolinafen, thiazopyr;
sulfonyl ureas selected from the group consisting of amidosulfuron, azimsulfuron, b en sul furon, chlorimuron-ethyl, chlorsulfuron, cinosulfuron, cyclosulfamuron, ethoxysulfuron, flazasulfuron, flucetosulfuron, flupyrsulfuron, foramsulfuron, halosulfuron, imazosulfuron, iodosulfuron, mesosulfuron, metazosulfuron, metsulfuron-methyl, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, 1-((2-chloro-6-propyl-imidazo[1,2-b]pyridazin-3-yl)sulfonyl)-3-(4,6-dimethoxy-pyrimidin-2-yl)urea;
triazines selected from the group consisting of ametryn, atrazine, cyanazine, dimethametryn, ethiozin, hexazinone, metamitron, metribuzin, prometryn, simazine, terbuthylazine, terbutryn, triaziflam;
ureas selected from the group consisting of chlorotoluron, daimuron, diuron, fluometuron, isoproturon, linuron, methabenzthiazuron, tebuthiuron;
acetolactate synthase inhibitors selected from the group consisting of bispyribac-sodium, cloransulam-methyl, diclosulam, florasulam, flucarbazone, flumetsulam, metosulam, ortho-sulfamuron, penoxsulam, propoxycarbazone, pyribambenz-propyl, pyribenzoxim, pyriftalid, pyriminobac-methyl, pyrimisulfan, pyrithiobac, pyroxasulfone, pyroxsulam, amicarbazone, aminotriazole, anilofos, beflubutamid, benazolin, bencarbazone, benfluresate, benzofenap, bentazone, benzobicyclon, bicyclopyrone, bromacil, bromobutide, butafenacil, butamifos, cafenstrole, carfentrazone, cinidon-ethyl, chlorthal, cinmethylin, clomazone, cumyluron, cyprosulfamide, dicamba, difenzoquat, diflufenzopyr, *Drechslera monoceras*, endothal, ethofume sate, etobenzanid, fenoxasulfone, fentrazamide, flumicloracpentyl, flumioxazin, flupoxam, flurochloridone, flurtamone, indanofan, isoxaben, isoxaflutole, lenacil, propanil, propyzamide, quinclorac, quinmerac , mesotrione, methyl arsonic acid, naptalam, oxadiargyl, oxadiazon, oxaziclomefone, pentoxazone, pinoxaden, pyraclonil, pyraflufen-ethyl, pyrasulfotole, pyrazoxyfen, pyrazolynate, quinoclamine, saflufenacil, sulcotrione, sulfentrazone, terbacil, tefuryltrione, tembotrione, thiencarbazone, topramezone, (3-[2-chloro-4- fluoro-5-(3-methyl-2,6-dioxo-4-trifluoromethyl-3,6-dihydro-2H-pyrimidin-1-yl)-phenoxy]-pyridin-2-yloxy)-acetic acid ethyl ester, 6-amino-5-chloro-2-cyclopropyl-pyrimidine-4-carboxylic acid methyl ester, 6-chloro-3-(2-cyclopropyl-6-methyl-phenoxy)-pyridazin-4-ol, 4-amino-3-chloro-6-(4-chloro-phenyl)-5-fluoro-pyridine-2-carboxylic acid, 4-amino-3-chloro-6-(4-chloro-2-fluoro-3-methoxy-phenyl)-pyridine-2-carboxylic acid methyl ester, and 4-amino-3-chloro-6-(4-chloro-3-dimethylamino-2-fluoro-phenyl)-pyridine-2-carboxylic acid methyl ester and combinations thereof.

10. The method set forth in claim 8 wherein the herbicide is selected from the group consisting of pendimethalin, dimethenamid-P, and a combination of pendimethalin and dimethenamid-P.

11. The method set forth in claim 10 wherein the herbicide is a combination of pendimethalin and dimethenamid-P and wherein the ratio of pendimethalin to dimethenamid-P is in the range of 1:10 to 5:1 based on the weight of the components.

12. The method set forth in claim 1 wherein the functional additive comprises an insecticide.

13. The method set forth in claim 12 wherein the insecticide is selected from thiodicarb, alpha-cypermethrin, clothianidin, imidacloprid, thiamethoxam, thiacloprid, dinotefuran, GABA antagonist compounds, fipronil, cyazypyr, rynaxapyr, and combinations thereof.

14. The method set forth in claim 1 wherein the functional additive comprises a fungicide.

15. The method set forth in claim 14 wherein the fungicide is selected from strobilurins selected from the group consisting of azoxystrobin, pyraclostrobin, trifloxystrobin, carboxamides selected from the group consisting of boscalid, fluopyram, fluxapyroxad, penflufen, penthiopyrad, sedaxane, C14 demethylase inhibitors selected from the group consisting of difenoconazole, ipconazole, prothioconazole, triticonazole, phenylamides, acyl amino acid fungicides selected from the group consisting of metalaxyl and metalaxyl-M, thiabendazole, ethaboxam, oxathiapiprolin, thiocarbamates, dithiocarbamates, mancozeb, phthalimides, sulfamides, chloronitriles, nitrapyrin, oxathiapiprolin and combinations thereof.

16. The method set forth in claim 1, wherein the functional additive comprises a biological.

17. The method set forth in claim 16 wherein the biological is selected from the group consisting of *Bacillus subtilis, Bacillus subtilis* FB17, *Bacillus amyloliquefaciens, Bacillus amyloliquefaciens* FZB42, *B. amyloliquefaciens* IN937a, *B. amyloliquefaciens* IT-45, *B. amyloliquefaciens* TJ1000, *B. amyloliquefaciens* ssp. *plantarum* MBI600, *B. cereus* CNCM I-1562, *B. firmus* CNCM I-1582, *Bacillus pumilus* KFP9F, *B. pumilus* QST 2808, *Bradyrhizobium japonicum, Coniothyrium minitans* CON/M/91-08, *Pasteuria nishizawae* Pn1, *Penicillium bilaiae, Pseudomonas fluorescens* CL 145A, *Rhizobium leguminosarum* bv. *phaseoli, Rhizobium leguminosarum* bv. *trifolii* RP113-7, *Rhizobium leguminosarum* bv. *viciae* P1NP3Cst, *Rhizobium leguminosarum* bv. *viciae* SU303, *Rhizobium leguminosarum* bv. *viciae* WSM1455, *Sinorhizobium meliloti* MSDJ0848, *Trichoderma fertile* JM41R, and combinations thereof.

18. The method set forth in claim 1 further comprising delivering a flow of colorant to a plurality of spray nozzles within the mixing chamber and operating at least one of the plurality of spray nozzles to direct an atomized spray of colorant into the mixing chamber for contact with particulate landscaping material in the mixing chamber.

19. The method set forth in claim 1 wherein the additive mixture further comprises a colorant.

20. The method set forth in claim 1 wherein the additive mixture comprises at least two functional additives.

* * * * *